(12) United States Patent
Wright et al.

(10) Patent No.: US 7,302,164 B2
(45) Date of Patent: Nov. 27, 2007

(54) SYSTEM AND METHOD FOR PRODUCING MEDICAL IMAGE DATA ONTO PORTABLE DIGITAL RECORDING MEDIA

(75) Inventors: Ken Wright, Chino Hills, CA (US); Chet LaGuardia, Rancho Santa Margarita, CA (US)

(73) Assignee: Datcard Systems, Inc., Irvine, CA (US)

( * ) Notice: Subject to any disclaimer, the term of this patent is extended or adjusted under 35 U.S.C. 154(b) by 945 days.

(21) Appl. No.: 09/761,795

(22) Filed: Jan. 17, 2001

(65) Prior Publication Data

US 2002/0048222 A1 Apr. 25, 2002

Related U.S. Application Data

(60) Provisional application No. 60/181,985, filed on Feb. 11, 2000.

(51) Int. Cl.
H04N 5/91 (2006.01)
(52) U.S. Cl. .................. 386/95; 386/112; 386/126
(58) Field of Classification Search ............ 386/46, 386/95, 125, 126; 600/407; 709/219; 705/2
See application file for complete search history.

(56) References Cited

U.S. PATENT DOCUMENTS 4,491,725 A 1/1985 Pritchard (Continued)

FOREIGN PATENT DOCUMENTS

DE 198 02 572 A 1 8/1999

(Continued)

OTHER PUBLICATIONS

XP-000914152 Haufe, et al., PACS at Work: A Multimedia E-Mail Tool for the Inegration of Images, Voice and Dynamic Annotation, Computer Assisted Radiology (1996).

(Continued)

Primary Examiner—Huy Nguyen
(74) Attorney, Agent, or Firm—Knobbe, Martens Olson & Bear LLP

(57) ABSTRACT

This application discloses a system for recording medical image data for production on a portable digital recording medium such as CDs and DVDs. This system includes a receiving module, a processing module and an output module, with viewing program for viewing medical image data stored on the portable digital recording medium. It also discloses a method of storing medical image data on a portable digital recording medium, including the steps of receiving the medical image data, processing the data and storing the data on the portable digital recording medium, with a viewing program for viewing medical image data stored on the portable digital recording medium. It further discloses a method of selecting medical image data for recording on a portable digital recording medium, including the steps of connecting a browsing terminal to a computer database that stores the medical image data, selecting a first set of the medical image data from the computer database, and recording the selected first set of medical image data on the portable digital medium, with a viewing program for viewing the medical image data stored on the portable digital recording medium. It also discloses the method and system of retrieving medical image data that are related to the received/selected original medical image data, and recording the original and related medical image data on a portable digital recording medium.

27 Claims, 5 Drawing Sheets

U.S. PATENT DOCUMENTS

| | | | |
|---|---|---|---|
| 4,852,570 A | 8/1989 | Levine | |
| 4,860,112 A | 8/1989 | Nichols et al. | |
| 4,874,935 A | 10/1989 | Younger | |
| 4,945,410 A | 7/1990 | Walling | |
| 4,958,283 A | 9/1990 | Tawara et al. | |
| 5,002,062 A | 3/1991 | Suzuki | |
| 5,005,126 A | 4/1991 | Haskin | |
| 5,019,975 A | 5/1991 | Mukai | |
| 5,208,802 A | 5/1993 | Suzuki et al. | |
| 5,235,510 A | 8/1993 | Yamada et al. | |
| 5,272,625 A | 12/1993 | Nishihara et al. | |
| 5,291,399 A | 3/1994 | Chaco | |
| 5,321,520 A | 6/1994 | Inga et al. | |
| 5,321,681 A | 6/1994 | Ramsay et al. | |
| 5,384,643 A | 1/1995 | Inga et al. | |
| 5,410,676 A | 4/1995 | Huang et al. | |
| 5,416,602 A | 5/1995 | Inga et al. | |
| 5,451,763 A | 9/1995 | Pickett et al. | |
| 5,469,353 A | 11/1995 | Pinsky et al. | |
| 5,499,293 A | 3/1996 | Behram et al. | |
| 5,513,101 A | 4/1996 | Pinsky et al. | |
| 5,531,227 A | 7/1996 | Schneider | |
| 5,542,768 A | 8/1996 | Rother et al. | |
| 5,544,649 A | 8/1996 | David et al. | |
| 5,586,262 A | 12/1996 | Komatsu et al. | |
| 5,597,182 A | 1/1997 | Reber et al. | |
| 5,597,995 A | 1/1997 | Williams et al. | |
| 5,605,153 A | 2/1997 | Fujioka et al. | |
| 5,655,084 A | 8/1997 | Pinsky et al. | |
| 5,659,741 A | 8/1997 | Eberhardt | |
| 5,671,353 A | 9/1997 | Tian et al. | |
| 5,687,717 A | 11/1997 | Halpern et al. | |
| 5,724,582 A | 3/1998 | Pelanek et al. | |
| 5,734,629 A | 3/1998 | Lee et al. | |
| 5,734,915 A | 3/1998 | Roewer | |
| 5,763,862 A | 6/1998 | Jachimowicz et al. | |
| 5,796,862 A | 8/1998 | Pawlicki et al. | |
| 5,809,243 A | 9/1998 | Rostoker et al. | |
| 5,822,544 A | 10/1998 | Chaco et al. | |
| 5,823,948 A | 10/1998 | Ross, Jr. et al. | |
| 5,832,488 A | 11/1998 | Eberhardt | |
| 5,848,198 A | 12/1998 | Penn | |
| 5,859,628 A | 1/1999 | Ross et al. | |
| 5,867,795 A | 2/1999 | Novis et al. | |
| 5,867,821 A | 2/1999 | Ballantyne et al. | |
| 5,869,163 A | 2/1999 | Smith et al. | |
| 5,873,824 A | 2/1999 | Doi et al. | |
| 5,882,555 A | 3/1999 | Rohde et al. | |
| 5,884,271 A | 3/1999 | Pitroda | |
| 5,899,998 A | 5/1999 | McGauley et al. | |
| 5,909,551 A * | 6/1999 | Tahara et al. | 709/231 |
| 5,911,687 A | 6/1999 | Sato et al. | |
| 5,914,918 A | 6/1999 | Lee et al. | |
| 5,924,074 A | 7/1999 | Evans | |
| 5,942,165 A | 8/1999 | Sabatini | |
| 5,946,276 A | 8/1999 | Ridges et al. | |
| 5,950,207 A | 9/1999 | Mortimore et al. | |
| 5,982,736 A | 11/1999 | Pierson | |
| 5,995,077 A | 11/1999 | Wilcox et al. | |
| 5,995,345 A | 11/1999 | Overbo | |
| 5,995,965 A | 11/1999 | Experton | |
| 6,006,191 A | 12/1999 | DiRienzo | |
| 6,021,404 A | 2/2000 | Moukheibir | |
| 6,022,315 A | 2/2000 | Iliff | |
| 6,032,120 A | 2/2000 | Rock et al. | |
| 6,041,703 A | 3/2000 | Salisbury et al. | |
| 6,063,030 A | 5/2000 | Vara et al. | |
| 6,067,075 A | 5/2000 | Pelanek | |
| 6,241,668 B1 | 6/2001 | Herzog | |
| 6,260,021 B1 * | 7/2001 | Wong et al. | 705/2 |
| 6,272,470 B1 | 8/2001 | Teshima | |
| 6,363,392 B1 | 3/2002 | Halstead et al. | |
| 6,397,224 B1 | 5/2002 | Zubeldia et al. | |
| 6,415,295 B1 | 7/2002 | Feinberg | |
| 6,564,256 B1 * | 5/2003 | Tanaka | 709/219 |
| 6,671,714 B1 | 12/2003 | Weyer et al. | |
| 6,954,802 B2 * | 10/2005 | Sutherland et al. | 710/5 |
| 2002/0085476 A1 | 7/2002 | Samari-Kermani | |
| 2002/0103811 A1 | 8/2002 | Fankhauser et al. | |
| 2002/0138524 A1 | 9/2002 | Ingle et al. | |
| 2004/0078236 A1 * | 4/2004 | Stoodley et al. | 705/2 |
| 2006/0179112 A1 | 8/2006 | Weyer et al. | |

FOREIGN PATENT DOCUMENTS

| | | |
|---|---|---|
| EP | 0 684 565 A1 | 11/1995 |
| EP | 0 781 032 A2 | 6/1997 |
| EP | 0 952 726 A1 | 10/1999 |
| GB | 2096440 | 10/1982 |

OTHER PUBLICATIONS

Terry May, "Medical Information Security: The Evolving Challenge", © 1998, IEEE pp. 85-92.

Ted Cooper, "Kaiser Permanente Anticipates High Cost as it Gears up for HIPPA", IT health Care Strategist, vol. 1, No. 10, Oct. 1999, p. 4.

Medical Imaging Magazine, Jan. 2000. Product Showcase, Automated Dicom Exchange Station. 1 page.

Dimitroff D C et al: "An Object Oriented Approach to Automating Patient Medical Records" Proceedings of the International Computer Software And Applications Conference. (Compsac), US, Washington, IEEE. Comp. Soc. Press, vol. CONF. 14, 1990, pp. 82-87.

Kleinholz L et al: "Multimedia and PACS, Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996, pp. 313-322, XP002083080 1996, Amsterdam, Netherlands, Elsevier, Netherlands ISBN: 0-444-82497-9.

* cited by examiner

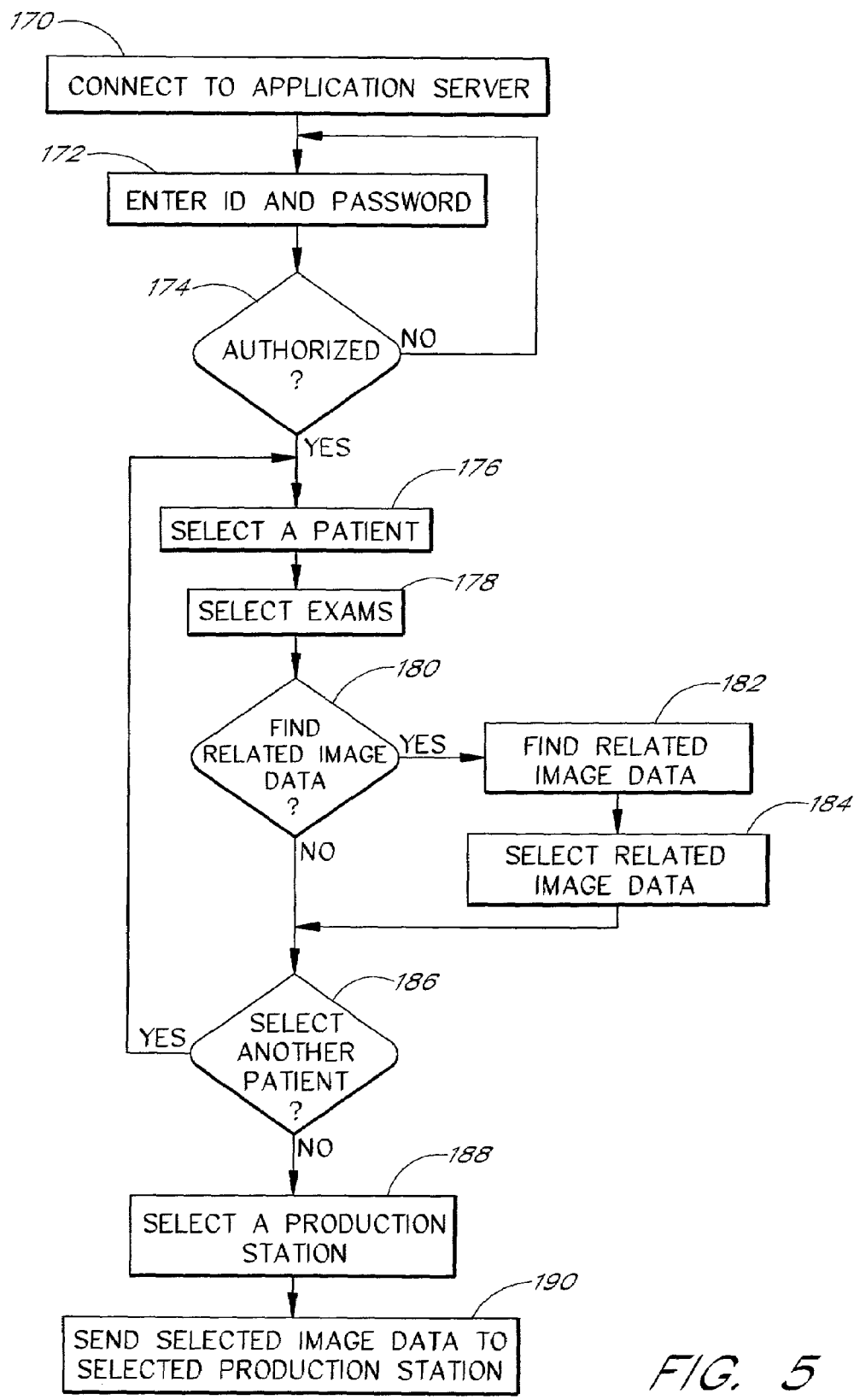

SYSTEM AND METHOD FOR PRODUCING MEDICAL IMAGE DATA ONTO PORTABLE DIGITAL RECORDING MEDIA

CROSS REFERENCE TO RELATED APPLICATIONS

This non-provisional application claims priority date from the provisional patent application Ser. No. 60/181,985, titled "Medical Information System" and filed Feb. 11, 2000.

BACKGROUND OF THE INVENTION

1. Field of the Invention

This invention relates to a system and method for the production of medical image data on portable digital recording media such as compact discs. More particularly, it relates to a system and method for receiving medical image data, processing medical image data, and transmitting medical image data to be recorded on a portable digital recording medium.

2. Description of the Related Art

Since the invention of the x-ray film, film has been the predominant multipurpose medium for the acquisition, storage, and distribution of medical images. However, the storage and distribution of film often requires considerable expenses in labor and storage space.

Today's modern hospitals utilize computer-aided imaging devices such as Computed Tomography (CT), Digital Subtracted Angiography, and Magnetic Resonance Imaging (MRI). These digital devices can generate hundreds of images in a matter of seconds. Many hospitals require these images to be printed on film for storage and distribution. To print complete sets of medical images from these digital devices, the cost in film material, storage space, and management efforts is often very high.

Some radiology departments have installed digital image storage and management systems known as PACS (Picture Archive Communication Systems). PACS are capable of storing a large amount of medical image data in digital form. PACS are made by manufacturers including GE, Siemens, and Fuji.

To ease the communication of data, the DICOM (Digital Imaging and Communications in Medicine) standard was developed by ACR-NEMA (American College of Radiology-National Electrical Manufacturer's Association) for communication between medical imaging devices and PACS. In addition to the examined images, patient demographics, and exam information such as patient name, patient age, exam number, exam modality, exam machine name, and exam date can also be stored and retrieved in DICOM compatible data format. A DICOM file stores patient and exam information in the header of the file, followed by the exam images. PACS store medical image data in DICOM format.

Digital medical image data can be stored on PACS and distributed using the Internet. However, many physicians' offices do not have the bandwidth suitable for fast download of medical image data. The concerns for medical data privacy and Internet security further reduce the desirability of Internet distribution.

SUMMARY OF THE INVENTION

The claimed system allows for digital medical image data to be produced on a portable digital recording medium such as a CD. A CD containing the medical image data can be distributed to physicians, hospitals, patients, insurance companies, etc. One embodiment of the claimed system allows for medical image data to be placed on a CD along with a viewing program, so that a user can use any computer compatible with the CD to view the medical image data on the CD. One embodiment of the claimed system allows for searching medical exam data that are related and placing such data on the same CD.

One embodiment of the claimed system comprises a receiving module configured to receive medical image data, a processing module configured to process the received medical image data, and an output module configured to transmit the processed medical image data to a production station configured to produce the transmitted medical image data on portable digital recording medium, such as a CD. In one embodiment, the output module transmits a viewing program configured to view medical image data to the production station so that the viewing program is produced on the same CD as the medical image data. In another embodiment, the CD already contains the viewing program before the medical image data is transmitted to the CD production station.

In one embodiment of the claimed system, the processing module is configured to create and store audit information of the portable digital recording medium produced by the production station.

In another embodiment of the claimed system, the processing module is configured to identify the originating image input device of the received medical image data, and determine, on the basis of the originating image input device, whether to transmit the received medical image data to a production station. The processing module also selects, on the basis of the originating image input device, one of multiple production stations as the target production station.

Yet another embodiment of the claimed system is configured to retrieve medical image data that are related to the received medical image data, and transmit the retrieved related image data to the production station. In one embodiment, exam images of the same patient are considered related. In another embodiment, exam images of the same patient and the same modality are considered related. For example, two x-ray exams on the left hand of the same patient are considered related. In yet another embodiment, exam images of the same patient, the same modality and taken within a specified date range are considered related. For example, two x-ray exams on the left hand of the same patient taken within a two-month period are considered related. A hospital may also determine other scenarios of relatedness.

One claimed method comprises the steps of connecting a browsing terminal to a computer database configured to store medical image data, selecting medical image data from medical image data stored on the database, and recording the selected medical image data on portable digital recording medium. In one embodiment, the claimed method also comprises a step of recording a viewing program configured to view medical image data on the portable digital recording medium.

One embodiment of the claimed method further comprises the steps of finding and retrieving medical image data that are related to the selected medical image data, and recording related image data to portable digital recording medium.

BRIEF DESCRIPTION OF THE DRAWINGS

FIG. 5 illustrates a process of a user selecting and ordering the production of image data stored on the application server, with the option of selecting and ordering the production of related image data.

DETAILED DESCRIPTION OF THE PREFERRED EMBODIMENT

Figure 1:
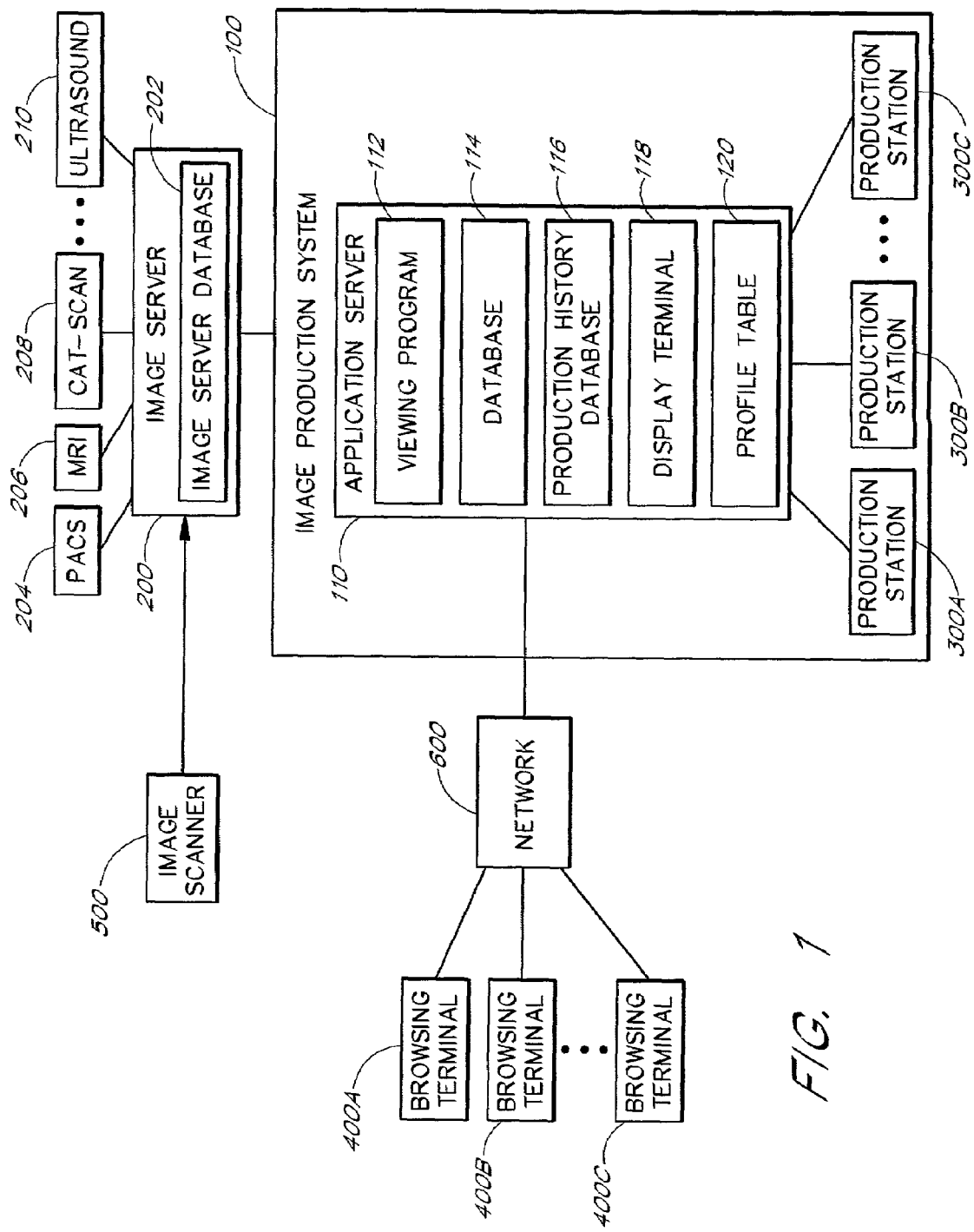
FIG. 1 illustrates one embodiment of an image production system comprising an application server and portable digital recording medium production stations.

FIG. 1 illustrates one embodiment of an image production system 100 comprising an application server 110 and one or more portable digital recording medium production stations 300A, 300B and 300C. In the preferred embodiment, the production stations 300A, 300B and 300C are CD (Compact Disc) production stations. Digital portable recording medium comprises CDs and DVDs (Digital Versatile Disc or Digital Video Disc). CDs may comprise CD-ROM (Compact Disc Read Only Memory), CD-R (Compact Disc Recordable), and CD-RW (Compact Disc Recordable and Writable). DVDs may comprise DVD-ROM (DVD Read Only Memory), DVD-R (DVD Recordable) and DVD-RAM (a standard for DVDs that can be read and written many times). Thus, although the following description refers primarily to CDs, those of ordinary skill in the art will understand that any suitable portable digital recording medium can be substituted for CDs.

The application server 110 is connected to one or more physician browsing terminals 400A, 400B and 400C through a computer network 600. Each physician browsing terminal 400A, 400B or 400C comprises a browsing program such as Internet Explorer or Netscape Communicator. Physicians or their assistants launch the browsing program to access the application server 110 through the network 600 in order to select medical image data stored on the application server database 114 to be produced by a production station 300A, 300B or 300C. In the preferred embodiment, the physician browsing terminals 400A, 400B and 400C are connected to the application server through an Intranet. One embodiment of the Intranet utilizes TCP/IP network protocol. The Intranet can connect one radiology department, multiple departments within a hospital, or multiple hospitals. In another embodiment the browsing terminals 400A, 400B and 400C are connected to the application server 110 through the Internet.

Still referring to FIG. 1, the application server 110 is also connected to an image server 200. The image server 200 is further connected to image input devices such as PACS 204, MRI machines 206, CT-scan machines 208, ultrasound machines 210, etc. In the preferred embodiment, the image server 200 is a DICOM image server configured to receive and store medical image data in DICOM format. In operation, the image server 200 receives medical image data from image input devices such as PACS 204, MRI machines 206, CT-scan machines 208 and ultrasound machines 210 and stores such image data in the image server database 202. A high-resolution image scanner 500 is also connected to the image server 200, so that medical image data stored on film can be scanned on the image scanner 500, transmitted to the image server 200 and stored in the image server database 202. In one embodiment, the image scanner 500 also converts the scanned image to DICOM format. The application server 110 receives input image data from the image server database 202, processes the received image data, and sends the image data to one of the production stations 300A, 300B or 300C to produce CDs.

The application server 110 comprises a viewing program 112, an application server database 114 that stores image data received from the image server 200, a production history database 116 that stores audit records on each CD produced, a display terminal 118 for programming and operating the application server 110 by a programmer or physician, and an image input device profile table 120.

Still referring to FIG. 1, the viewing program 112 is configured to allow users to read and manipulate medical image data. The viewing program 112 comprises multiple image manipulation functions, such as rotating images, zooming in and zooming out, measuring the distance between two points, etc. The viewing program 112 also allows users to read the patient demographics and exam information associated with the image data. The viewing program 112 used in the preferred embodiment is produced by eFilm Medical Inc. located in Toronto, Canada. The viewing program 112 used in the preferred embodiment is an abbreviated version with fewer functions and takes less storage space, in order to maximize the storage space for image data on a CD. The image server 200 used in the preferred embodiment is also made by eFilm Medical Inc.

The CD production stations 300A, 300B and 300C in the preferred embodiment are produced by Rimage Corporation in Edina, Minn. Details about the Rimage CD production stations can be found in U.S. Pat. Nos. 5,542,768, 5,734,629, 5,914,918, 5,946,276, and 6,041,703, which are incorporated herein by reference in their entirety.

The application server 110 in the preferred embodiment runs on a personal computer running a 400 MHz Celeron or Pentium II/III chip, with Windows 98 or NT as the operating system.

Figure 2:
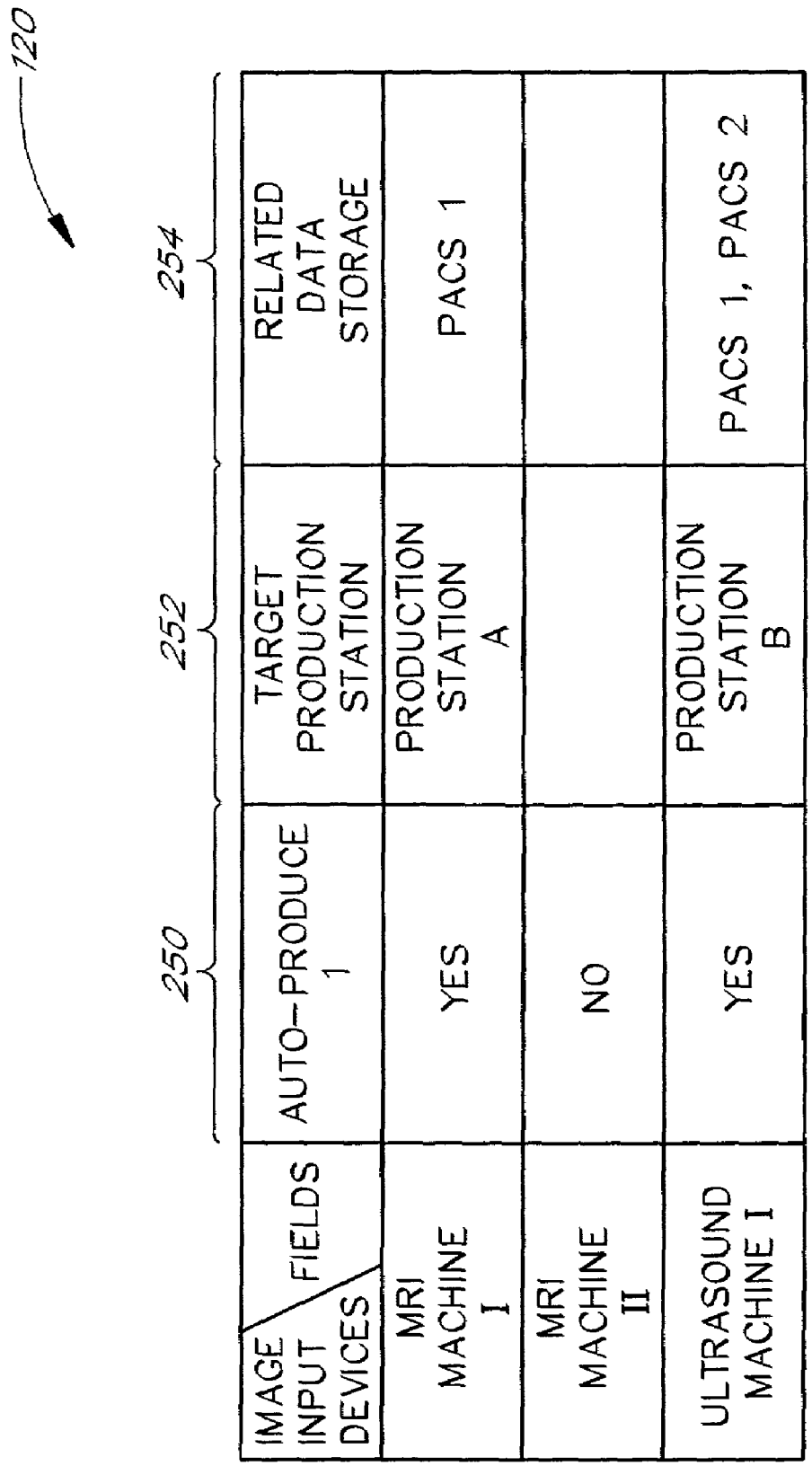
FIG. 2 illustrates sample records of one embodiment of an image input device profile table.

FIG. 2 illustrates sample records of one embodiment of an image input device profile table 120. The image input device profile table 120 contains a profile record for each image input device. Each image input device's profile record comprises: (1) an "auto-produce" logical field 250 indicating whether medical image data from this image input device should be produced on CD automatically by the image production system 100, (2) a "target production station" field 252 identifying one of the production stations 300A, 300B or 300C on which medical image data is to be produced, and (3) a "related data storage" 254 field identifying the medical image data storage units in which to search for the related image data. A medical image data storage unit is a storage unit that stores medical image data and is connected to the application server 110. In one embodiment, a medical image data storage unit is connected to the application server 110 through the image server 200. In the preferred embodiment, PACS 204 is such a medical image data storage unit.

In FIG. 2, the sample profile table 120 contains profile records for MRI Machine I, MRI Machine II, and Ultrasound Machine I. For MRI Machine I, the "auto-produce" field 250 contains a "yes" value, directing the image production system 100 to automatically produce image data originating from MRI Machine I on portable digital recording medium. Its "target production station" field 252 contains a "Production Station A" value, directing the image production system 100 to produce image data originating from MRI Machine I on production station A. Its "related data storage" field 254 is "PACS I", directing the image production system 100 to retrieve related medical image data from PACS I. For MRI Machine II, the "auto-produce" field 250 is "no", directing the image production system 100 to not automatically produce image data originating from MRI Machine II on portable digital recording medium. Since image data from MRI Machine II will not be automatically produced, the "target production station" field 252 and the "related data storage" field 254 are irrelevant. For Ultrasound Machine I, the "auto-produce" field 250 is "yes", and its "target production" filed 252 is "Production Station B". Its "related data storage" field 254 contains a value of "PACS I, PACS II", directing the image production system 100 to search PACS I and PACS II for related medical image data.

Figure 3:
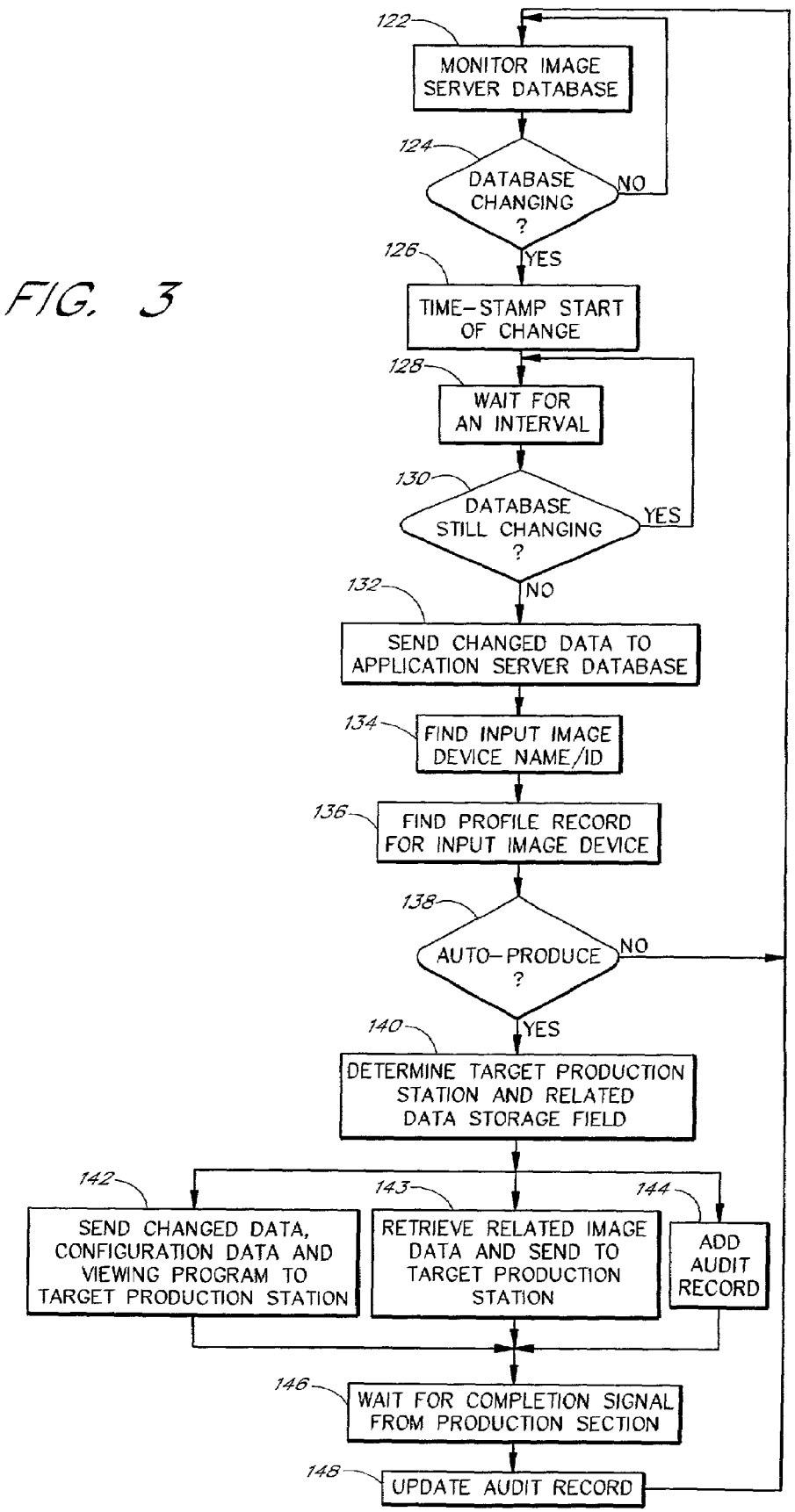
FIG. 3 illustrates a process of receiving image data from image server, processing received image data, and transmitting such data to the production station. This process also retrieves and transmits related image data for production.

FIG. 3 illustrates a process of the application server 110 receiving image data from the image server 200, processing the received image data, and transmitting such data to the production station 300A, 300B or 300C. The application server 110 continuously monitors the image server database 202 in step 122. In one embodiment, the application server 110 continuously "pings" the network address corresponding to the image server 200 on the network that connects the application server 110 with the image server 200.

Still referring to FIG. 3, the application server 110 determines if the image server database 202 is changing, in step 124. In the preferred embodiment, the application server 110 makes that determination by detecting whether the image server database 202 is increasing in size. If there is no change in the image server database 202, then the application server 110 returns to step 122 to continue monitoring. If there is change in the image server database 202, then the application server 110 proceeds to step 126 and time-stamps the moment that the change started. The application server 110 then proceeds to step 128 and waits for an interval, typically 35 to 65 seconds. After the interval, the application server 110 checks whether the image server database 202 is still changing, in step 130. If the image server database 202 is still changing then the application server 110 returns to step 128 to wait for another interval. If the image server database 202 is no longer changing, then the application server 110 proceeds to step 132 and copies the data changed since the time-stamped moment. This changed data is copied from the image server database 202 to the application server database 114.

The application server 110 proceeds to step 134 and finds the input image device name or identification number from the newly received image data. In the preferred embodiment, image data from the image server database 202 are stored in DICOM format, and the input image device name or identification number is stored in the header of the DICOM format image data file. The input image device name/ID indicates the origin of the newly received data. The application server 110 proceeds to step 136 and uses the found input image device name/ID to find a corresponding profile record in the image input device profile table 120. If the profile record has an "auto-produce" field 250 with a "no" value, the application server 110 returns from step 138 to step 122 to continue monitoring the image server database 202. If the "auto-produce" field 250 contains a "yes" value, the application server 110 proceeds from step 138 to step 140, and determines the target production station 300A, 300B or 300C from the "target production station" field 252 of the profile record. In step 140, the application server 110 also determines the value in the "related data storage" field 254 of the profile record.

Still referring to FIG. 3, in step 142, the application server 110 sends a copy of the newly received data, along with a copy of the viewing program 112, to the target production station 300A, 300B or 300C identified in step 140. With the viewing program attached, the image data on each CD produced by the target production station 300A, 300B or 300C can be viewed on any computer that accepts the CD, regardless of whether that computer has its own viewing program installed. In one embodiment, the data received in step 132 is stored in the application server database 114 before it is transmitted to the target production station 300A, 300B or 300C in step 142. In another embodiment, the application server 110 transmits the data received in step 132 to the target production station 300A, 300B or 300C, without storing a copy of the data in the application server database 114.

In one embodiment, the application server 110 does not send a copy of the viewing program 112 to the target production station during step 142. Rather, the application server 110 sends a copy of the received medical image data to the production station 300A, 300B or 300C to be recorded on pre-burned CDs. Each pre-burned CD contains a viewing program already recorded onto the CD before step 142.

In step 142, the application server 110 also sends configuration data to the target production station 300A, 300B or 300C. The configuration data comprises a label-printing file comprising the specification for printing labels on top of the CDs, and a "number of copies" value indicating the number of copies of CDs to be produced. A typical specification in the label-printing file may specify information such as patient name, exam modality, hospital name, physician name, production date, etc. to be printed by the target production station as a label on the top of each CD produced.

Still referring to FIG. 3, in step 143, the application server 110 searches the application server database 114 for image data related to the newly received data. The application server 110 then searches the PACS systems identified in the "related data storage" field 254 in step 140 for data related to the newly received data. Some PACS systems each comprise a primary image data storage and an archive image data storage, and the application server 110 searches both the primary image data storage and the archive image data storage on these PACS systems. The application server 110 is connected to the PACS systems through the image server 200. The application server 110 retrieves found related data from the PACS systems and stores a copy of such found related data in the application server database 114. The application server 110 sends a copy of related data that are found from the application server database 114 or the PACS systems to the target production station 300A, 300B or 300C. The medical image data originally received in step 132 and the related medical image data are produced by the target production station 300A, 300B or 300C on the same CDs for comparative study.

For each CD to be produced, the application server 110 adds one audit record to the production history database 116 in step 144. The new audit record comprises the identification number of the CD and other relevant information about the CD, such as the physician who requested the production (if any), and the names of the patients whose exam images are on that CD.

Steps 142, 143 and 144 may be executed immediately before, concurrent with, or immediately after one another.

The target production station 300A, 300B or 300C produces the CDs containing the medical image data and the viewing program sent to it, and prints a label on top of every CD, corresponding to the specification in the label-printing file. The number of CDs produced corresponds to the "number of copies" number sent by the application server 110 in step 142. When the target production station has produced the CDs, the production station returns a "completed" signal to the application server 110. The application server 110 waits for this signal in step 146.

Still referring to FIG. 3, in step 148, the application server 110 updates the audit records in the production history database 116 that were created in step 144. For each CD produced, the application 110 server updates the date and time of production for that CD's audit record. The application server 110 also updates the status value for that CD's audit storage record from "processing" to "successful". The application server 110 then continues monitoring the image server database 202 as in step 122.

Figure 4:
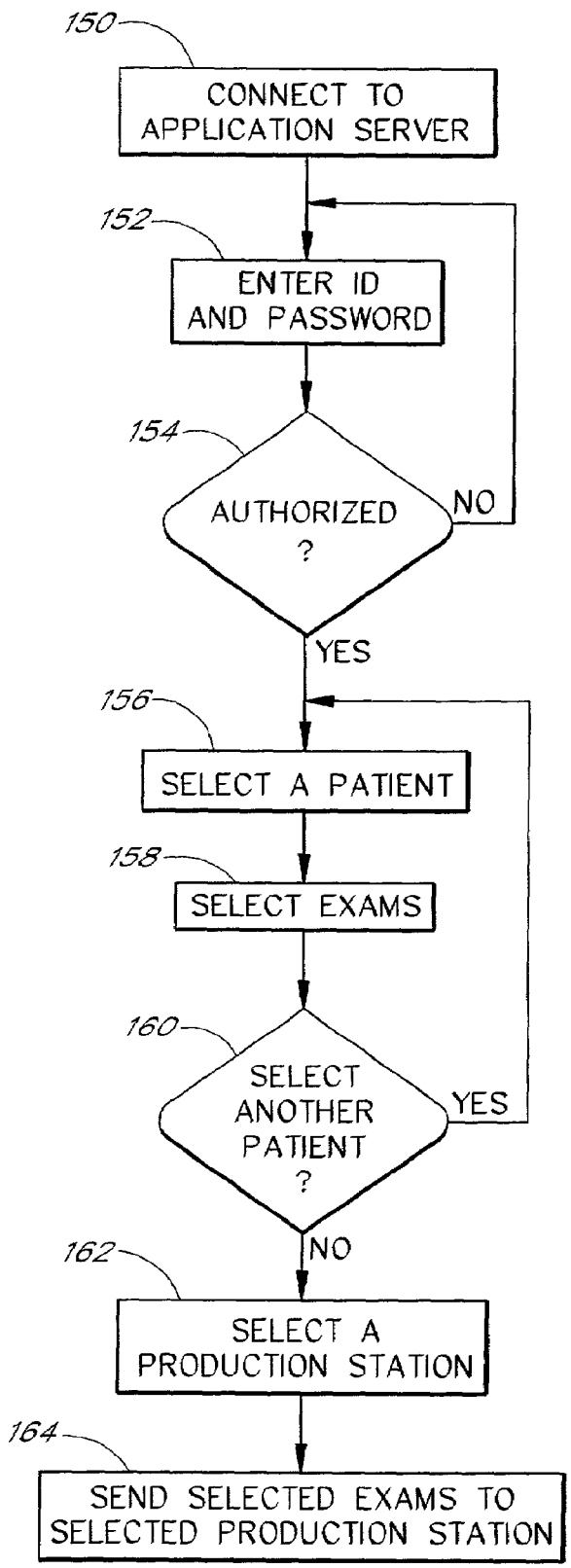
FIG. 4 illustrates a process of a user selecting and ordering the production of image data stored on the application server.

FIG. 4 illustrates a process of a user selecting and ordering the production of image data stored on the application server 110. A user, typically a physician or physician's assistant, accesses the application server database 114 from a browsing terminal 400A, 400B or 400C connected to a network 600. In one embodiment, the user launches a browser such as Microsoft Internet Explorer or Netscape Communicator, and specifies a network address corresponding to the application server 110, in step 150. In another embodiment, the user clicks a pre-defined icon that directly launches a browser connecting to the application server 110. The application server 110 prompts the user to enter a password or an identification name coupled with a password, in step 152. The application server 110 checks if the entered identification/password is authorized in step 154. If the entered identification/password is not authorized the user is returned to step 152 to re-enter the identification/password, or disconnected from the application server 110. If the entered identification/password is authorized then the user is allowed access to the application server database 114 and the application server 110 proceeds to step 156.

Still referring to FIG. 4, in step 156 the user is prompted to select a patient from a list of patients with exam images in the application server database 114. The user is then shown a list of the selected patient's exams, and is prompted to select one or more exams of that patient, in step 158. When the user indicates that he/she has completed selecting all exams for that patient, the user is asked in step 160 whether to select another patient from the list of patients. If the user answers "yes", the user is returned to step 156 to select another patient. If the user answers "no", the user proceeds to step 162.

In another embodiment, when a user selects a patient, all exams belonging to that patient will be automatically selected without prompting for user selection. In yet another embodiment, the user is not prompted to select patients, but is only prompted to select exams from a list of all exams for all patients contained in the application server database 114.

When the user indicates that he/she has completed selecting, the user is prompted to select a production station from a list of production stations 300A, 300B and 300C in step 162. The user is also prompted to enter additional label text to be printed as labels on the CDs to be produced, to supplement the text printed according to the specification of the label-printing file. The user can advantageously select the production station located closest to his/her office. In one embodiment, only one production station is connected to the application server 110, and the lone production station will be the selected production station without prompting for user selection.

In one embodiment, the user is also prompted to select the number of copies of CDs to be produced. In another embodiment, the number of copies is set at one without prompting for user direction. As described above in connection with FIG. 3, in step 164, the application server 110 sends a copy of the image data of the selected exams for the selected patients to the selected production station, along with a copy of the viewing program 112, and configuration data comprising a label-printing file, additional label text, and a number indicating the number of copies of CDs to be produced. The production station 300A, 300B or 300C then produces one or more CDs containing the selected exams for the selected patients and the viewing program, with labels printed on top of the CDs according to the specification in the label-printing file and the user-entered additional label text.

In another embodiment, a user accesses the application server database 114 not from a browsing terminal 400A, 400B or 400C, but directly from the display terminal 118. In this embodiment the user directly proceeds from step 152. In this embodiment the user is typically a programmer or operator of the image production system 100.

FIG. 5 illustrates a process of a user selecting and ordering the production of image data stored on the application server 110, with the additional option of selecting and ordering the production of related data for comparative study. As described above in connection with FIG. 4, a user connects to the application server 110 from a browsing terminal 400A, 400B or 400C in step 170. The user enters identification information and a password in step 172. Step 174 determines whether the user is authorized to access the application server database 114. If authorized, the user is prompted to select a patient in step 176, and selects exams of the selected patient in step 178. The user is then asked in step 180 if he/she desires to find related data of that patient for comparative study.

If the user answers yes, the application server 110 then searches for related data. The application server 110 finds the image input device profile table 120 profile record corresponding to the image input device from which the selected data originates, identifies the list of PACS systems stored in the "related data storage" field 254, and searches these PACS systems for related data. In another embodiment, once the user has selected a patient/exam combination, the application server 110 automatically searches for related data without asking for user direction. In this embodiment, the application server 110 alerts the user if related data are found. In one embodiment, the application server 110 also searches the application server database 114 for related medial image data.

Still referring to FIG. 5, the user is then prompted to select all or some of the related data from the list of found related data for production, in step 184. In another embodiment, all found related data are automatically selected by the application server 110 for production, without prompting for user selection.

The user is then prompted to select another patient in step 186. After the user has completed selecting all patients, the user is prompted to select a CD production station 300A, 300B or 300C in step 188. The user is also prompted to enter additional label text. In step 190, the application server 110 then sends a copy of the original and selected related data, along with a copy of the viewing program 112, a number indicating the number of copies to be produced, additional label text, and a label-printing file to the selected production station 300A, 300B or 300C for production.

The above paragraphs describe the application server 110 with one database 114 for image data storage. In another embodiment, the application server 110 includes two databases for image data storage: a new data database and a storage data database. The new data database stores only the most recent batch of new data just received from the image server 200. After the data in the new data database is sent to a production station 300A, 300B or 300C, the application server 110 erases data in the new data database. The storage data database stores all data that has ever been received from the image server database 202. In the processes described by FIG. 4 and FIG. 5, a user selects images for production from the storage data database.

Several modules are described in the specification and the claims. The modules may advantageously be configured to reside on an addressable storage medium and configured to execute on one or more processors. The modules may include, but are not limited to, software or hardware components that perform certain tasks. Thus, a module may include, for example, object-oriented software components, class components, processes methods, functions, attributes, procedures, subroutines, segments of program code, drivers, firmware, microcode, circuitry, data, databases, data structures, tables, arrays, and variables. Modules may be integrated into a smaller number of modules. One module may also be separated into multiple modules.

Although the foregoing has been a description and illustration of specific embodiments of the invention, various modifications and changes can be made thereto by persons skilled in the art, without departing from the scope and spirit of the invention as defined by the following claims.

What is claimed is:

1. A system for selecting and automatically recording medical image data onto a data storage medium, the system being connected to a medical image server, the system comprising:
    an application server;
    a plurality of production stations;
    a plurality of browsing terminals;
    a network connecting the application server, the plurality of production stations and the plurality of browsing terminals, wherein the application server is configured to receive medical image data from the medical image server, the medical images received being formatted in a standard medical imaging format used by specialized computers configured for viewing medical images, the application server further comprising:
        a selection module configured to allow a user to select selected medical image data via at least one of (a) a selected one of the plurality of browsing terminals and (b) the application server,
        a search module configured to automatically search the medical image server for related medical image data that is related to the selected medical image data,
        a configuration data module configured to allow a user to input identifying information relating to the selected medical image data,
        a production station selection module configured to allow a user to select one of the plurality of production stations, wherein the selected production station is configured to receive the selected medical image data and the related medical image data to produce a data storage medium that has recorded on it the selected and the related medical image data, the selected medical image data being recorded on the data storage medium in the standard medical imaging format, and
        an audit module configured to automatically provide an auditable trail of the selected medical image data;
    a viewing program for the standard medical imaging format that is recorded on the data storage medium, and that is configured to allow viewing of medical image data stored on the data storage medium on widely accessible computers not specifically configured with standard medical imaging software for viewing of medical images; and
    a label automatically printed and applied to the data storage medium at the production station, the label containing the identifying information.

2. The system of claim 1, wherein the data storage medium is an optical disk.

3. The system of claim 1, wherein the auditable trail of the selected medical image data includes a record of when the selected medical image data and the related medical image data were recorded onto the data storage medium.

4. The system of claim 1, wherein the medical image server is configured to provide medical image data to the application server in response to generation of medical image data by an imaging modality coupled to the medical image server.

5. The system of claim 4, wherein the imaging modality is an image scanner configured to generate medical image data in a DICOM-compatible format from a film.

6. The system of claim 1, wherein the application server further comprises a user authentication module configured to authenticate a user's identification before the user is allowed to access the selection module.

7. The system of claim 1, wherein the application server further includes a database configured to store medical image data received from the medical image server.

8. The system of claim 7, wherein the selection module is further configured to provide the user with a listing of patients having medical image data stored in the database.

9. A system comprising:
    a medical image server configured to receive medical image data that is generated by a plurality of imaging modalities, the medical image data being formatted in a standard medical imaging format used by specialized computers configured for viewing medical images;
    a database configured to store medical image data generated by the plurality of imaging modalities;
    a plurality of browsing terminals configured to receive a user selection that defines selected medical image data;
    a search module configured to search the database for related medical image data that is related to the selected medical image data; and
    a production station that is configured to record all of the following onto a data storage medium:
        the selected medical image data, recorded in the standard medical imaging format,
        the related medical image data, recorded in the standard medical imaging format, and
        a viewing program that is configured to allow viewing of the selected and the related medical image data that is recorded onto the data storage medium on widely accessible computers not specifically configured with standard medical imaging software for viewing of medical images.

10. The system of claim 9, further comprising a configuration data module configured to allow a user to input identifying information relating to the selected medical image data.

11. The system of claim 10, wherein the production station is further configured to print and apply a label to the data storage medium, the label containing the identifying information.

12. The system of claim 9, further comprising an audit module that is configured to automatically provide an auditable trail of the selected medical image data.

13. The system of claim 12, wherein the auditable trail of the selected medical image data includes a record of when the selected medial image data and the related medical image data were recorded onto the data storage medium.

14. The system of claim 12, wherein the auditable trail of the selected medical image data includes identifying information corresponding to the production station used to record the selected medial image data and the related medical image data onto the data storage medium.

15. The system of claim 9, wherein the data storage medium is an optical disk.

16. A method for selecting and automatically recording medical image data onto a data storage medium, the method comprising:
receiving medical image data from a plurality of imaging modalities, the received medical image data being formatted in a standard medical imaging format used by specialized computers configured for viewing medical images;
storing the received medical image data in a database;
providing a user interface configured to receive a user selection that defines selected medical image data;
searching the database for related medical image data that is related to the selected medical image data;
recording the selected medical image data and the related medical image data onto a data storage medium using a production station, the selected medical image data being recorded on the data storage medium in the standard medical imaging format;
recording a viewing program onto the data storage medium using the production station, the viewing program being configured to allow viewing of medical image data stored on the data storage medium on widely accessible computers not specifically configured with standard medical imaging software for viewing of medical images;
printing a label using the production station, wherein the label includes identifying information associated with the selected medical image data; and
affixing the label to the data storage medium using the production station.

17. The method of claim 16, further comprising generating an auditable trail of the selected medical image data, wherein the auditable trail includes a record of when the selected medial image data and the related medical image data were recorded onto the data storage medium.

18. The method of claim 16, wherein the user interface is further configured to collect the identifying information from the user.

19. The method of claim 16, further comprising providing, via the user interface, a list of patients having medical image data stored in the database.

20. The method of claim 16, wherein the plurality of imaging modalities includes an image scanner configured to generate medical image data in a DICOM-compatible format from a film.

21. The method of claim 16, wherein the data storage medium is an optical disk.

22. The method of claim 16, wherein recording the selected medical image data and the related medical image data further comprising selecting a selected production station from a plurality of production stations that are connected to the database via a computer network.

23. A system comprising:
an application server configured to receive medical image data from a medical image server, wherein the medical image data is received in a standard medical imaging format used by specialized computers configured for viewing medical images;
a plurality of production stations;
a plurality of browsing terminals; and
a network connecting the application server, the plurality of production stations and the plurality of browsing terminals;
wherein the application server comprises:
a selection module configured to allow a user to select selected medical image data via a user interface,
a search module configured to search the medical image server for related medical image data that is related to the selected medical image data, and
a production station selection module configured to allow a user to select one of the plurality of production stations, wherein the selected production station is configured to (a) receive the selected medical image data and the related medical image data, (b) produce a data storage medium that has recorded thereon in the standard medical imaging format the selected medical image data and the related medical image data, and (c) also record onto the data storage medium a viewing program for the standard medical imaging format that is configured to allow viewing of the selected medical image data and the related medical image data on widely accessible computers with standard medical imaging software for viewing medical images.

24. The system of claim 23, wherein the selection module is configured to allow the user to select selected medical image data using a selected one of the plurality of production stations or a selected one of the plurality of browsing terminals.

25. The system of claim 23, wherein the application server further comprises a configuration data module configured to allow the user to input identifying information relating to the selected medical imaging data.

26. The system of claim 25, further comprising a label applied to the data storage medium, the label containing the identifying information.

27. The system of claim 23, wherein the application server further comprises an audit module configured to provide an auditable trail of the selected medical image data.

* * * * *

UNITED STATES PATENT AND TRADEMARK OFFICE
CERTIFICATE OF CORRECTION

| | | |
|---|---|---|
| PATENT NO. | : 7,302,164 C1 | Page 1 of 1 |
| APPLICATION NO. | : 90/009347 | |
| DATED | : January 4, 2011 | |
| INVENTOR(S) | : Ken Wright et al. | |

It is certified that error appears in the above-identified patent and that said Letters Patent is hereby corrected as shown below:

In Column 1, Line 40, in Claim 9, after "portable" insert --*digital*--.

In Column 1, Line 40, in Claim 9, delete "medium" and insert --[medium] *device that is removable from the production station*--.

In Column 1, Line 47, in Claim 9, delete "medium" and insert -- [medium] *device*--.

In Column 1, Line 67, in Claim 15, delete ":" and insert -- ; --.

In Column 2, Line 27, in Claim 16, delete "portable" and insert --*portable, digital*--.

In Column 2, Line 28, in Claim 16, delete "medium" and insert --[medium] *device*--.

In Column 2, Line 30, in Claim 16, delete "medium" and insert --[medium] *device*--.

In Column 2, Line 32, in Claim 16, delete "medium" and insert --[medium] *device*--.

In Column 2, Line 34, in Claim 16, delete "medium" and insert --[medium] *device*--.

In Column 2, Line 40, in Claim 16, after "data;" delete "and" and insert --[and]--.

In Column 2, Line 41, in Claim 16, delete "medium" and insert --[medium] *device*--.

In Column 2, Line 42, in Claim 16, delete "production station." and insert --production station; *removing the data storage device from the production station.*--.

Signed and Sealed this
Nineteenth Day of April, 2011

David J. Kappos
*Director of the United States Patent and Trademark Office*

US007302164C1

(12) EX PARTE REEXAMINATION CERTIFICATE (7967th)
United States Patent
Wright et al.

(10) Number: US 7,302,164 C1
(45) Certificate Issued: Jan. 4, 2011

(54) SYSTEM AND METHOD FOR PRODUCING MEDICAL IMAGE DATA ONTO PORTABLE DIGITAL RECORDING MEDIA

(75) Inventors: Ken Wright, Chino Hills, CA (US); Chet LaGuardia, Rancho Santa Margarita, CA (US)

(73) Assignee: Datcard Systems, Inc., Newport Beach, CA (US)

Reexamination Request:
No. 90/009,347, Nov. 26, 2008

Reexamination Certificate for:
Patent No.: 7,302,164
Issued: Nov. 27, 2007
Appl. No.: 09/761,795
Filed: Jan. 17, 2001

Related U.S. Application Data
(60) Provisional application No. 60/181,985, filed on Feb. 11, 2000.

(51) Int. Cl.
H04N 5/91 (2006.01)

(52) U.S. Cl. .................. 386/95; 386/112; 386/126
(58) Field of Classification Search ........................ None
See application file for complete search history.

(56) References Cited

U.S. PATENT DOCUMENTS

| | | |
|---|---|---|
| 4,491,725 A | 1/1985 | Pritchard |
| 4,736,256 A | 4/1988 | Ichikawa |
| 4,768,099 A | 8/1988 | Mukai |
| 4,852,570 A | 8/1989 | Levine |
| 4,860,112 A | 8/1989 | Nichols et al. |
| 4,874,935 A | 10/1989 | Younger |
| 4,945,410 A | 7/1990 | Walling |

(Continued)

FOREIGN PATENT DOCUMENTS

| | | |
|---|---|---|
| CA | 2322191 | 4/2000 |
| DE | 198 02 572 A1 | 8/1999 |
| EP | 0 684 565 A1 | 11/1995 |
| EP | 0 781 032 A3 | 3/1999 |
| EP | 0 952 726 A1 | 10/1999 |
| GB | 2 096 440 A | 10/1982 |
| JP | 04-177473 A | 6/1992 |
| JP | 06-261892 A | 9/1994 |
| WO | WO 97/22297 | 6/1997 |
| WO | WO 00/02202 | 1/2000 |
| WO | WO 00/1925416 | 4/2000 |

OTHER PUBLICATIONS

"Med–volviz–faq–2000–01," dated Jan. 2000.
"Med–volviz–faq–98–11," dated Nov. 1998.

(Continued)

*Primary Examiner*—Sam Rimell

(57) ABSTRACT

This application discloses a system for recording medical image data for production on a portable digital recording medium such as CDs and DVDs. This system includes a receiving module, a processing module and an output module, with viewing program for viewing medical image data stored on the portable digital recording medium. It also discloses a method of storing medical image data on a portable digital recording medium, including the steps of receiving the medical image data, processing the data and storing the data on the portable digital recording medium, with a viewing program for viewing medical image data stored on the portable digital recording medium. It further discloses a method of selecting medical image data for recording on a portable digital recording medium, including the steps of connecting a browsing terminal to a computer database that stores the medical image data, selecting a first set of the medical image data from the computer database, and recording the selected first set of medical image data on the portable digital medium, with a viewing program for viewing the medical image data stored on the portable digital recording medium. It also discloses the method and system of retrieving medical image data that are related to the received/selected original medical image data, and recording the original and related medical image data on a portable digital recording medium.

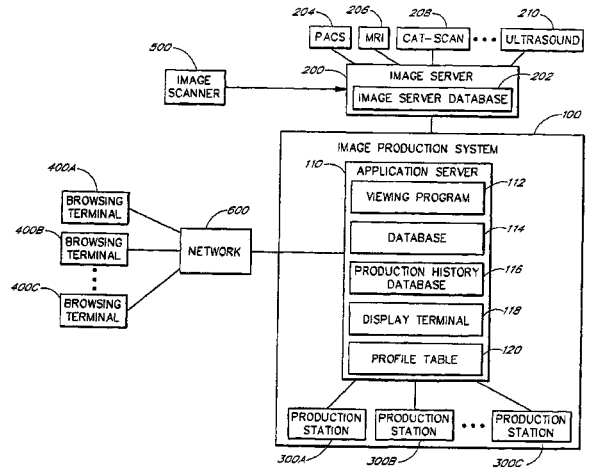

U.S. PATENT DOCUMENTS

| | | |
|---|---|---|
| 4,958,283 A | 9/1990 | Tawara et al. |
| 5,002,062 A | 3/1991 | Suzuki |
| 5,005,126 A | 4/1991 | Haskin |
| 5,019,975 A | 5/1991 | Mukai |
| 5,208,802 A | 5/1993 | Suzuki et al. |
| 5,235,510 A | 8/1993 | Yamada et al. |
| 5,272,625 A | 12/1993 | Nishihara |
| 5,291,399 A | 3/1994 | Chaco |
| 5,317,337 A | 5/1994 | Ewaldt |
| 5,319,543 A | 6/1994 | Wilhelm |
| 5,321,681 A | 6/1994 | Ramsay et al. |
| 5,384,643 A | 1/1995 | Inga et al. |
| 5,410,676 A | 4/1995 | Huang et al. |
| 5,451,763 A | 9/1995 | Pickett et al. |
| 5,452,416 A | 9/1995 | Hilton et al. |
| 5,469,353 A | 11/1995 | Pinsky et al. |
| 5,499,293 A | 3/1996 | Behram et al. |
| 5,502,726 A | 3/1996 | Fischer |
| 5,513,101 A | 4/1996 | Pinsky et al. |
| 5,518,325 A | 5/1996 | Kahle |
| 5,531,227 A | 7/1996 | Schneider |
| 5,542,768 A | 8/1996 | Rother |
| 5,544,649 A | 8/1996 | David et al. |
| 5,572,422 A | 11/1996 | Nematbakhsh et al. |
| 5,581,460 A | 12/1996 | Kotake et al. |
| 5,586,262 A | 12/1996 | Komatsu et al. |
| 5,592,511 A | 1/1997 | Schoen et al. |
| 5,597,182 A | 1/1997 | Reber et al. |
| 5,597,995 A | 1/1997 | Williams et al. |
| 5,605,153 A | 2/1997 | Fujioka et al. |
| 5,633,839 A | 5/1997 | Alexander et al. |
| 5,634,053 A | 5/1997 | Noble et al. |
| 5,655,084 A | 8/1997 | Pinsky et al. |
| 5,659,741 A | 8/1997 | Eberhardt |
| 5,668,998 A | 9/1997 | Mason et al. |
| 5,671,353 A | 9/1997 | Tian et al. |
| 5,687,717 A | 11/1997 | Halpern et al. |
| 5,717,841 A | 2/1998 | Farrell et al. |
| 5,721,891 A | 2/1998 | Murray |
| 5,724,582 A | 3/1998 | Pelanek et al. |
| 5,734,629 A | 3/1998 | Lee et al. |
| 5,734,915 A | 3/1998 | Roewer |
| 5,740,134 A | 4/1998 | Peterson |
| 5,763,862 A | 6/1998 | Jachimowicz et al. |
| 5,781,221 A | 7/1998 | Wen et al. |
| 5,796,862 A | 8/1998 | Pawlicki et al. |
| 5,809,243 A | 9/1998 | Rostoker et al. |
| 5,822,544 A | 10/1998 | Chaco et al. |
| 5,823,948 A | 10/1998 | Ross, Jr. et al. |
| 5,832,488 A | 11/1998 | Eberhardt |
| 5,848,198 A | 12/1998 | Penn |
| 5,859,628 A | 1/1999 | Ross et al. |
| 5,867,795 A | 2/1999 | Novis et al. |
| 5,867,821 A | 2/1999 | Ballantyne et al. |
| 5,869,163 A | 2/1999 | Smith et al. |
| 5,873,824 A | 2/1999 | Doi et al. |
| 5,882,555 A | 3/1999 | Rohde et al. |
| 5,884,271 A | 3/1999 | Pitroda |
| 5,899,998 A | 5/1999 | McGauley et al. |
| 5,909,551 A | 6/1999 | Tahara et al. |
| 5,911,687 A | 6/1999 | Sato et al. |
| 5,914,918 A | 6/1999 | Lee et al. |
| 5,920,317 A | 7/1999 | McDonald |
| 5,924,074 A | 7/1999 | Evans |
| 5,942,165 A | 8/1999 | Sabatini |
| 5,946,216 A | 8/1999 | Hollerich |
| 5,946,276 A | 8/1999 | Ridges et al. |
| 5,949,491 A | 9/1999 | Callahan et al. |
| 5,950,207 A | 9/1999 | Mortimore et al. |
| 5,951,819 A | 9/1999 | Hummell et al. |
| 5,974,004 A | 10/1999 | Dockes et al. |
| 5,974,201 A | 10/1999 | Chang et al. |
| 5,982,736 A | 11/1999 | Pierson |
| 5,995,077 A | 11/1999 | Wilcox et al. |
| 5,995,345 A | 11/1999 | Overbo |
| 5,995,965 A | 11/1999 | Experton |
| 6,006,191 A | 12/1999 | DiRienzo |
| 6,021,404 A | 2/2000 | Moukheibir |
| 6,022,315 A | 2/2000 | Iliff |
| 6,032,120 A | 2/2000 | Rock et al. |
| 6,041,703 A | 3/2000 | Salisbury |
| 6,063,030 A | 5/2000 | Vara et al. |
| 6,067,075 A | 5/2000 | Pelanek |
| 6,115,486 A | 9/2000 | Cantoni |
| 6,137,527 A | 10/2000 | Abdel-Malek et al. |
| 6,149,440 A | 11/2000 | Clark et al. |
| 6,157,914 A | 12/2000 | Seto et al. |
| 6,188,782 B1 | 2/2001 | Le Beux |
| 6,241,668 B1 | 6/2001 | Herzog |
| 6,260,021 B1 | 7/2001 | Wong |
| 6,272,470 B1 | 8/2001 | Teshima |
| 6,363,392 B1 | 3/2002 | Halstead et al. |
| 6,366,966 B1 | 4/2002 | Laney et al. |
| 6,397,224 B1 | 5/2002 | Zubeldia et al. |
| 6,415,295 B1 | 7/2002 | Feinberg |
| 6,416,602 B1 | 7/2002 | Firatli |
| 6,454,705 B1 | 9/2002 | Cosentino et al. |
| 6,529,757 B1 | 3/2003 | Patel et al. |
| 6,564,256 B1 | 5/2003 | Tanaka |
| 6,564,336 B1 | 5/2003 | Majkowski |
| 6,574,629 B1 | 6/2003 | Cooke, Jr. et al. |
| 6,574,742 B1 | 6/2003 | Jamroga et al. |
| 6,606,171 B1 | 8/2003 | Renk et al. |
| 6,615,192 B1 | 9/2003 | Tagawa et al. |
| 6,633,674 B1 | 10/2003 | Barnes et al. |
| 6,654,724 B1 | 11/2003 | Rubin et al. |
| 6,671,714 B1 | 12/2003 | Weyer et al. |
| 6,675,271 B1 | 1/2004 | Xu et al. |
| 6,678,703 B2 | 1/2004 | Rothschild et al. |
| 6,678,764 B2 | 1/2004 | Parvulescu et al. |
| 6,760,755 B1 | 7/2004 | Brackett |
| 6,847,933 B1 | 1/2005 | Hastings |
| 6,910,038 B1 | 6/2005 | James |
| 6,925,319 B2 | 8/2005 | McKinnon |
| 6,954,767 B1 | 10/2005 | Kanada |
| 6,954,802 B2 | 10/2005 | Sutherland et al. |
| 6,988,074 B2 | 1/2006 | Koritzinsky et al. |
| 7,006,881 B1 | 2/2006 | Hoffberg et al. |
| 7,020,651 B2 | 3/2006 | Ripley |
| 7,111,015 B2 | 9/2006 | Aoyama |
| 7,120,644 B1 | 10/2006 | Canessa et al. |
| 7,194,119 B2 | 3/2007 | Zahlmann et al. |
| 7,268,794 B2 | 9/2007 | Honda et al. |
| 7,302,164 B2 | 11/2007 | Wright et al. |
| 7,382,255 B2 | 6/2008 | Chung et al. |
| 7,395,215 B2 | 7/2008 | Grushka |
| 7,483,839 B2 | 1/2009 | Mayaud |
| 2001/0041991 A1 | 11/2001 | Segal et al. |
| 2001/0056359 A1 | 12/2001 | Abreu |
| 2002/0007287 A1 | 1/2002 | Straube et al. |
| 2002/0019751 A1 | 2/2002 | Rothschild et al. |
| 2002/0046061 A1 | 4/2002 | Wright et al. |
| 2002/0077861 A1 | 6/2002 | Hogan |
| 2002/0085476 A1 | 7/2002 | Samari-Kermani |
| 2002/0103811 A1 | 8/2002 | Fankhauser et al. |
| 2002/0133373 A1 | 9/2002 | Silva-Craig et al. |
| 2002/0138301 A1 | 9/2002 | Karras et al. |
| 2002/0138524 A1 | 9/2002 | Ingle et al. |
| 2003/0051144 A1 | 3/2003 | Williams |
| 2003/0200226 A1 | 10/2003 | Wells et al. |
| 2003/0208382 A1 | 11/2003 | Westfall |

| | | | |
|---|---|---|---|
| 2004/0078236 A1 | 4/2004 | Stoodley et al. |
| 2004/0215637 A1 | 10/2004 | Kitamura et al. |
| 2005/0154614 A1 | 7/2005 | Swanson et al. |
| 2005/0197860 A1 | 9/2005 | Joffe et al. |
| 2005/0240445 A1 | 10/2005 | Sutherland et al. |
| 2005/0267351 A1 | 12/2005 | Humphrey et al. |
| 2006/0058626 A1 | 3/2006 | Weiss et al. |
| 2006/0149601 A1 | 7/2006 | Langhofer et al. |
| 2006/0161928 A1 | 7/2006 | Douglass et al. |
| 2006/0179112 A1 | 8/2006 | Weyer et al. |
| 2007/0050216 A1 | 3/2007 | Wright et al. |
| 2008/0122878 A1 | 5/2008 | Keefe et al. |
| 2008/0172254 A1 | 7/2008 | Rosenfeld et al. |
| 2008/0221920 A1 | 9/2008 | Courtney |
| 2009/0018871 A1 | 1/2009 | Essig et al. |
| 2009/0238540 A1 | 9/2009 | Wright et al. |
| 2009/0245754 A1 | 10/2009 | Wright et al. |
| 2009/0248750 A1 | 10/2009 | Wright et al. |
| 2009/0252479 A1 | 10/2009 | Wright et al. |
| 2009/0252480 A1 | 10/2009 | Wright et al. |

OTHER PUBLICATIONS

"TDF Corporation Announces Statement of Direction to Integrate Image Edition with IBM ImagePlus VisualInfo," TDF Corporation, Apr. 1, 1996.

Lee Mantelman, "TDF Launches ImageMail—A 'Fed.EXE' for Digital Documents," ;Magazine, Nov. 1996.

"Algotec to Introduce New Communication Tools for R Physicians at HIMSS 2000," Algotec [Retrieved from http://www.algotec.com/web/upload_files/New_Communications_Tools,htm on Jan. 25, 2008].

Minutes, DICOM Standards Committee, Jan. 19–20, 1999.

"Archium Digital Cardiac System: Enhanced Cath Department Productivity and Workflow," Camtronics Medical Systems [Retrieved from http://web.archive.org/web/19980711040910/camtronics.com/cardiology/archium.htm, on Feb. 26, 2008].

"Image Workstation DICOM Conformance Statement," Camtronics Medical Systems, Copyright 1999.

"NT100/NT 200 Network Imaging Systems," Camtronics Medical Systems, dated 1998 [Retrieved from http://web.archive.org/web/19980711040955/camtronics.com/network/nt.htm, on Feb. 26, 2008].

"About Camtronics," Camtronics Medical Systems, dated 1998 [Retrieved from http://web.archive.org/web/19980711040447/camtronics.com/about/main.htm, on Feb. 26, 2008].

"Digital Cardiac Archive and Review System Strategies," [Retrieved from http://web.archive.org/web/19980711041117/camtronics.com/cardiology/digital.htm, on Feb. 26, 2008].

"Cardiac Imaging Leaders Join Forces to Provide Image Network Solutions," dated Jul. 31, 1997, "New Digital Cardiac Imaging Upgrade Brings New Life To Exixting Cath Labs," dated Feb. 16, 1997, "Camtronics Introduces Three Archium Products Which Advance CD–R Exchange," dated Apr. 9, 1996 [Retrieved from http://web.archive.org/web/19980711041036/camtronics.com/news/news.htm, on Feb. 26, 2008].

"Antelope Valley Hospital Choosers Algotec for Full PACS Installation; Major Los Angeles County Hospital has History of Technological Innovation," Business Wire, dated Nov. 28, 2000.

TREX Medical Corp. Form 10–K, dated Dec. 6, 1996 [Retrieved from http://sec.edgar–online.com/1996/12/06/00/0001003539–96–000006/Section2.asp, on Feb. 20, 2008].

"DICOM—Digital Imaging and Communications in Medicine," Presentations of the European Society of Cardiology (ESC), dated Aug. 25, 1999.

Cardiac Imaging Issue, Newswatch, Mar. 2000 [Retrieved from http://www.mdeicalimaging.com/issues/articles/2000–03_10.asp?mode=print, on Feb. 22, 2008].

Erik L. Ridley, "Algotec Pursues ASP Model in Bid for PACS Market Success," AuntMinnie.com, dated May 2, 2000 [Retrieved from http://www.auntminnie.com/print/print.asp?sec=sup&sub=pac&pag=dis&ItemID=740&printpage=true, on Mar. 5, 2008].

Marie S. Marchese, "Algotec: Where the Web PACS Punch," Nuclear Medicine, Jun. 2000 Issue [Retrieved from http://www.medicalimagingmag.com/issues/articles/2000–06_11.asp, on Jan. 25, 2008].

Product Overview Webpage, DR Systems, Inc., dated Jan. 26, 1998 [Retrieved from http://web.archive.org/web/19981202142228/www.dominator.com/products.htm, on Mar. 6, 2008].

Image Edition Product Webpage, The TDF Product Line, TDF Corp., Copyright 1997.

Universal Manager Product Webpages, DR Systems, Inc., dated Jan. 26, 1998 [Retrieved from http://web.archive.org/web/19990218141212/www.dominator.com/prod02.htm, on Mar. 6, 2008].

Reading Station with Ambassador Product Webpage, DR Systems, Inc., dated Jan. 26, 1998.

Minutes, DICOM Standards Committee, Jun. 22–23, 1999.

David Hannon & Marie S. Marchese, "HIMSS Preview: HIMSS Brings New Features to Connectivity Carnival," Information Management, Apr. 2000 Issue [Retrieved from http://www.medicalimagingmag.com/issues/articles/2000–04_04.asp, on Mar. 3, 2008].

"DICOM Standards Committee: writeable CD–ROMs May Become Gold Standard of Image Exchange," Non–invasive Imaging, dated Feb. 1999.

Uwe Engelmann et al., "Borderless teleradiology with CHILI," Journal of Medical Internet Researc, dated Dec. 13, 1999 [Retrieved from http://www.jmir.org/1999/2/e8, on Mar. 3, 2008].

Gary R. Conrad, "A Simple Image Display Application for Windows," Journal of Digital Imaging, vol. 10, No. 3, pp. 115–119, Aug. 1997.

Ruediger Simon, "DICOM: State of the Standard in 1999."

DICOMwriter Single Lab Network Connections Product Webpage, Heartlab Products, Copyright 1999 [Retrieved from http://web.archive.org/web/19990417151612/www.heartlab.com/products/writer.cfm, on Mar. 3, 2008].

User's Manual for Medical Imaging and Communication System (Version 3), HiPax, Copyright 2000.

"New Solution Offers Film Copying to CD—View DICOM on Any PC," PR Newswire, dated Nov. 28, 2000.

"IBM Digital Library (developing information storage and retrieval system)," Newsline, dated May 1, 1995 [Retrieved from http://www.highbeam.com/DocPrint.aspx?DocId=1G1:17155094, on Mar. 5, 2008].

User's Guide for ImageAXS Pro–Med (Windows), Digital Arts & Sciences, Copyright 1998.

Mike Obstgarten, "Image Storage Devices & Media—New Magic," Advanced Imaging, Feb. 1, 1999 [Retrieved from http://www.highbeam.com/DocPrint.aspx?DocId=1G1:54116212, on Mar. 5, 2008].

DICOMwriter Product Webpage, Heartlab Inc., Copyright 1999.

"Smart and Friendly Ships Industry's Most Complete 4x CD Recorder Solution With CD–RW Rewritability; Complete CD–R/CD–RW Solution Features Support for DVD Compatibility, UDF–Compliant Direct Random Overwrite, and Recording from Vinyl Records and Cassette or 8 Track Tapes," Business Wire, dated Sep. 12, 1997 [Retrieved from http://www.encyclopedia.com/doc/1G1–19746834.html, on Feb. 14, 2008].

James L. Lear et al., "Redundant Array of Independent Disks: Practical On–Line Archiving of Nuclear Medicine Image Data," Journal of Digital Imaging, vol. 9, No. 1, pp. 37–38, Feb. 1996.

Amit Mehta et al., "Enhancing Availablity of the Electronic Image Record for Patients and Caregivers During Follow–Up Care," Journal of Digital Imaging, vol. 12, No. 2, pp. 78–80, May 1999.

Raffaele Noro et al., "Real–Time Telediagnosis of Radiological Images through an Asynchronous Transfer Mode Network: The ARTeMeD Project," Journal of Digital Imaging, vol. 10, No. 3, pp. 116–121, Aug. 1997.

Atsutoshi Oka et al., "Interhospital Network System Using the Worldwide Web and the Common Gateway Interface," Journal of Digital Imaging, vol. 12, No. 2, pp. 205–207, May 1999.

C.J. Henri et al., "Evolution of a Filmless Digital Imaging and Communications in Medicine–Conformant Picture Archiving and Communications System: Design Issues and Lessons Learned Over the Last 3 Years," Journal of Digital Imaging, vol. 12, No. 2, pp. 178–180, May 1999.

"Philips Introduces CD–Medical: The Digital Alternative to Cine Film," Business Wire, dated Mar. 20, 1995 [Retrieved from http://www.highbeam.com/DocPrint.aspx?DocId=1G1:16673959, on Mar. 5, 2008].

User Manual for Medimage: DICOM Archiving & Viewing Station, Vepro Computersyteme, dated May 9, 2000.

"A Virtual Image Bank," Yale Medicine, Winter/Spring 1998 [Retrieved from http://yalemedicine.yale.edu/ym_ws98/cover/cov_virtual05.html, on Feb. 10, 2008].

Mark Zaidel et al., "Interactive Web–Based Radiology Teaching File," Journal of Digital Imaging, vol. 12, No. 2, pp. 203–204, May 1999.

E–mail Communication B. M. Smka, gastrobase II, 1 page, Feb. 23, 2008.

James D. Thomas, "Digital Storage and Retrieval: The Future in EchoCardiography," Heart, 78, pp. 19–22, 1997.

James D. Thomas & Steven E. Nissen, "Digital Storage and Transmission of Cardiovascular Image: What are the Costs, Benefits and Timetable for Conversion?," Heart, 76, pp. 13–17, 1996.

"Acuson Releases ViewPro–Net Network Image Review Software Package," Acuson Corp., dated Mar. 8, 1999.

Ricky K. Taira et al., "A Concept–Based Retrieval System for Thoracic Radiology," Journal of Digital Imaging, vol. 9, No. 1, pp. 25–36, Feb. 1996.

Bradley J. Erickson et al., "READS: A Radiology–Oriented Electronic Analysis and Display Station," Journal of Digital Imaging, vol. 10, No. 3, pp. 67–69, Aug. 1997.

Erik L. Ridley, "Popularity of Windows NT Platform Continues to Grow as Vendors Standardize on Microsoft OS–NT, Web, and Integration Dominate PACS Exhibits," Diagnostic Imaging's WEBCAST of the 1998 RSNA Conference [Retrieved from http://www.dimag.com/webcast/wc_story.2htm, on Mar. 3, 2008].

Ramesh C. Verma et al., "Picture Archiving and Communication System—Asynchronous Transfer Mode Network in a Midsized Hospital," Journal of Digital Imaging, vol. 10, No. 3, pp. 99–102, Aug. 1997.

Edward M. Smith et al., "Project MICAS—Medical Information, Communication and Archive System: PACS Implementation at the University of Rochester Medical Center," Journal of Digital Imaging, vol. 10, No. 3, p. 228, Aug. 1997.

Hubert Chin et al., "Digital Photography of Digital Imaging and Communication in Medicine—3 Images From Computers in the Radiologist's Office," Journal of Digital Imaging, vol. 12, No. 2, pp. 192–194, May 1999.

E–mail Communication B. M. Srnka, CD RS, 1 page, Feb. 23, 2008.

Joseph G. Hennessey et al., "Digital Video Applications in Radiologic Education: Theory, Technique, and Applications," Journal of Digital Imaging, vol. 7, No. 2, pp. 85–90, May 1994.

Michael Abiri & Nanda Kirpekar, "Designing a Request for Proposal for Picture Archiving and Communication System," Journal of Digital Imaging, vol. 10, No. 3, pp. 20–23, Aug. 1997.

Richard K. Wertz, "CD–ROM: A New Advance in Medical Information Retrieval," JAMA, vol. 256, No. 24, pp. 3376–3378, Dec. 26, 1986.

Jean–Chrétien Oberson et al., "Development of an Electronic Radiologist's Office in a Private Institute," Radiographics, Copyright 2000 [Retrieved from http://radiographics.rsnajnls.org/cgi/content/full/20/2/573, on Mar. 3, 2008].

"CD–Medical Format for Cardiac Image Storage," Screen Digest, dated May 1, 1995 [Retrieved from http://www.highbeam.com/DocPrint.aspx?DocId=1G1:45516859, on Mar. 5, 2008].

Armond L. Levy et al., "An Internet–Connected, Patient–Specific, Deformable Brain Atlas Integrated into a Surgical Navigation System," Journal of Digital Imaging, vol. 10, No. 3, pp. 231–237, Aug. 1997.

"TDK Introduces Medical CD–R Recording Station," Business Wire dated Dec. 1, 1999 [Retrieved from http://findarticles.com/p/articles/mi_mOEIN/is_Dec_1/ai_57876529/print, on Mar. 11, 2008].

"PACS Companies Chase Referring Physicians," Diagnostic Imaging's RSNA Webcast [Retrieved from http://www.d-imag.com/webcast00/showArticle.ihtml?page=4.html on Mar. 5, 2008].

HIMSS.96—The 1996 Annual HIMSS Conference and Exhibition Disc, produced in *Datcard* v. *Codonics* Civil Action No. SACV 08–00063 AHS.

Product Showcase Webpage, Medical Imaging, Jan. 2000.

510(k) Summary of Safety and Effectiveness, Mitra Imaging, Inc., dated Oct. 31, 1997.

Cardiology Products Webpage, Eastman Kodak Co., Copyright 1994–1997.

Company Overview Webpage, Trex Medical Corp., Copyright 2000–2008.

510(k) Premarket Notification Database, MedImage Image Processing System, Vepro Computersyteme, dated Jun. 13, 1997.

CRS–PC / CRS–PC+ 1.3 Conformance Statement for DICOM V3.0, GE Medical Systems, Copyright 2000.

Guardian DICOM Archive Media Storage Conformance Statement, DR Systems, Inc., dated May 4, 1999.

Sienet MagicStore VB22D DICOM Conformance Statement, Siemens Health Services, dated May 11, 2000.

Ruediger Simon, "DICOM: State of the Standard in 1999," undated.

Tony Rickards, "What is DISC Birmingham 96!" Jul. 24, 1996.

"'Three–In–One: Siemens' SIENET MagicView 300 PACS Software Offers Image Distribution, Teleradiology and Mini–Archive," PRNewswire, Jun. 11, Copyright 1996–2008.

MedImage Image Management System DICOM Conformance Statement, Vepro, dated May 8, 2000.

SIENET Sky DICOM Conformance Statements Webpage, Siemens Healthcare, Copyright 2002–2008.

Acom.Convert DICOM Conformance Statements, Siemens, dated Sep. 15, 1999.

ARRI Oscar Product Brochure, ARRI, Copyright 1999.

L. Verhoeven and E. G. Mast, "Coronary X–ray Angiography: 40 Years of Experience," MedicaMundi, vol. 43, Iss. 2, Sep. 1999.

"Digital Imaging and Communications in Medicine (DICOM)," National Electrical Manufacturers Association, Copyright 1999.

Mary P. Anderson et al., "US Food and Drug Administration's Regulation of Software and Picture Archiving and Communication Systems," Journal of Digital Imaging, vol. 10, No. 3, p. 19, Aug. 1997.

Senographe 2000 D Review WorkStation DICOM V3.0 Conformance Statement, GE Medical Systems, Copyright 1999–2003.

Donald R. Cahill et al., "Sectional Anatomy Using the Personal Computer," Journal of Digital Imaging, vol. 10, No. 3, p. 227, Aug. 1997.

Siemens Sienet MagicView 50 Teleradiology System Webpage, Ovid Technologies, Inc. Copyright 2000–2007.

M. Desrosiers, "The Multimedia CD ROM: An Innovative Teaching Tool For Endoscpic Sinus Surgery," J Laparoendosc Adv. Surg. Tech. A, Aug. 1998.

R.D. Cox et al., "Transparent Image Access in a Distributed Picture Archiving and Communcations System: The Master Database Broker," Journal of Digital Imaging, vol. 12, No. 2, pp. 175–177, May 1999.

Letter from J. Hofmann re "MedImage—Digital Image and Document Management," 3 pages, Dec. 15, 1997.

UTech Product Brochure, UTech Products, Inc., dated Nov. 28, 1997.

Letter from T. Watson (Algotech) to M. Cannavo (Image Management Consultants), dated Apr. 8, 1998.

Imaginet Product Brochure, Algotec Systems, Copyright 1998.

Meta Solutions, Inc., *Meta Solutions, Inc.* (1998).

Accusoft, *High–Perfomance Medical Imaging Software* (1997).

Merge Technologies Incorporated, *Setting the Course for Electronic Image Management* (Feb. 1998).

OTech, *OTech News* vol. 2, Iss. 2 (1997).

Applicare Medical Imaging B.V., *The RadWorks Product Line Version 2.1 Product Catalog* (Summer 1997).

Linda A. Keska, *Letter re: Presentations* (Oct. 1, 1999).

David Avrin, *Radiology into the 21st Century: The Digital Department* (Sep. 8, 1999).

Douglas M. Tucker, *Archives* (Sep. 1999).

Radiology Service Partners, LLC, *Re–Engineering Radiology* (1997).

Siemens Health Services, *Sienet—DICOM Conformance Statement: MagicView 50 Versions VA10A, VA10B and VA10C Revision* 2.0 (Nov. 13, 1997).

Siemens Medical Systems, Inc., *PACS Planning & Integration Services* (1998).

Siemens Medical Systems, Inc., *Fast, secure, reliable Sienet Enterprise PACS* (1998).

Siemens Medical Systems, Inc., *MagicView 300 Enterprise–wide clinician viewing of images and reports* (1998).

Siemens Medical Systems, Inc., *MagicView 1000 Softcopy reading with advanced 3D processing customized to your preferences* (1998).

Siemens Medical Systems, Inc. *MagicView CT/MR* (1999).

Camtronics Medical Systems, *Service Manual Image Workstation Series* (1999).

H.K. Huang, *PACS: Basic Principles and Applications*, Wiley, New York (1999).

The Imaging Resource, *The Imaging Resource Digital Photography Newsletter*, vol. 1, No. 3 (Oct. 22, 1999).

Philips Medical Systems, *DICOM Conformance Statement—CD–Medical Recorder for DCI Systems CDM 3300—Release 1.1* (Oct. 31, 1996).

Philips Medical Systems, *510(k) Summary* (Sep. 23, 1999).

Daniel G. Schultz, *Letter re: 510(k) Notification* (Dec. 21, 1999).

Imaging Resource, *Kodak Picture CD*, http://www.imaging–resource.com/PRODS/PCD/PCDA.HTM (Nov. 10, 1999).

Adobe Systems, *Kodak Picture CD Reviewer's Guide*.

Adobe, *Adobe Opens the Digital Door to Visually Enhancing the Web with a Complete Family of Digital Imaging Products* (Jun. 17, 1999).

Sonya Donaldson, *Kodak Picture CD—Software Review—Evaluation* (Oct. 2000).

VEPRO Computersysteme GmbH, *MedImage The Image Management System—ACOM.Convert DICOM Archiving & Viewing Station, Software Vers. 4.42* (May 9, 1999).

VEPRO, *Certificate for the Quality Assurance System* (Feb. 12, 2004).

VEPRO Computersysteme, *Email re: MedImage Cardio/Angio Viewings Station; MedImage Image Server; MedImage CD–ROM Jukebox Server; MedImage DICOM 3.0 Server Akquisition Station; Cardio—Viewing Station; MedImage Digital Filmrecording & CD–R Archiving Station* Dec. 22, 1997).

VEPRO, *17 Years Computer Experience; Company Profile; Letter re: Software Evaluation; Email re: Software Evaluation* (Feb.–Mar. 1998).

VEPRO Computersysteme GmbH, *510(K) Summary* (Jun. 6, 1997).

Lillian Yin, *Letter re: 510(k) Notification* (Nov. 19, 1997).

U.S. Department of Health and Human Services, Food amd Drug Administration, Center for Devices and Radiological Health, *Guidance for Industry—Guidance for the Submission of Premarket Notifications for Medical Image Management Devices* (Jul. 27, 2000).

Jack I. Eisenman, "Book Review—PACS Basic Principles and Applications", *Radiology* (Jul. 1999).

K. Faulkner, "Book Review—PACS Basic Principles and Applications,", *The British Journal of Radiology* (Jul. 1999).

VEPRO Computersysteme GmbH, *MedImage The Image Management System—DICOM Archiving & Viewing Station, Software Version 4.42* (Jan. 26, 2000).

VEPRO Computersysteme GmbH, *MedImage The Image Management System—Digital Film Recording Station, Software Version 4.40* (Oct. 28, 1999).
VEPRO, *Viewing Software Handbook Viewing Software Version 4.41* (Oct. 7, 1998).
Tony Rickards, *DICOM Tutorial: ESC Annual Meeting Birmingham* (Aug. 1996).
TDK Medical, *Quotation and Technical Specification: TDK's CDRS–1100AD* (Jul. 17, 2003).
TDK Medical, *Quotation and Technical Specification: TDK's CDRS–1100AUTOTP* (Jul. 17, 2003).
TDK Medical, *Medical CD Recording Station Planning and Installation Manual* (2001).
KBMC Productions, *CDRS–1100AUTOTP Operator's Manual* (2002).
Siemens Medical Systems, Inc., *ACOM.M/B 2.2 Basic System DICOM Conformance Statement* (May 21, 1999).
Siemens Medical Systems, Inc., *ACOM.CONVERT DICOM Conformance Statement* (Sep. 15, 1999).
Siemens Medical Systems, Inc., *ACOM.Report VA01A DICOM Conformance Statement* (Sep. 17, 1999).
Siemens Medical Systems, Inc., *ACOM.Web VA21A DICOM Conformance Statement* (Mar. 9, 2000).
Siemens Medical Systems, Inc., *ACOM.Web VA21C DICOm Conformance Statement* (Mar. 21, 2001).
Siemens Medical Systems, Inc., *ACOM.Report VA02A DICOM Conformance Statement* (Dec. 21, 2001).
TREXnet HR Price Bok, dated 2000.
D. Farber et al., Camtronics IWS Open Issues List, updated Aug. 26, 1999.
TREXnet HR DICOM Medica Conference Statement, Trex Medical Corp., dated Jun. 29, 1998.
"SPEC, DICOM Interface, TREXnet HR to IWS," Trex Medical Corp., 2 pages, dated 1999.
"SPEC, DICOM Interface, TREXnet HR to IWS," Trex. Medical Corp., 4 pages, dated 1999.
"SPEC, FUNC, TREXnet HR Image Network," Trex Medical Corp., 42 pages, revised Jan. 25, 2000.
"SPEC, FUNC, TREXnet HR, Phase I," Trex Medical Corp., 29 pages, revised Jan. 12, 1999.
Huang, H.K., D.Sc. "PACS Basic Principles and Applications," Wiley–Liss, Inc. 1999, Title page, Copyright Notice page, Table of Contents, Chapter 7, Sections 10.5 and 12.5.
Mehta, A. et al., "Enhancing Availability of the Electronic Image Record for Patients and Caregivers During Follow–Up Care," Journal of Digital Imaging, vol. 12, No. 2, Supp. 1, May, 1999, pp. 78–80.
MedImage ACOM.Convert DICOM Archiving & Viewing Station Software Vers. 4.42 User Manual, Sep. 5, 1999.
Jean–Chrëtien Oberson et al., "Development of an Electronic Radiologist's Office in a Private Institute," Radiographics, Copyright 2000 [Retrieved from http://radiographics.rsnajnLs.org/cgi/content/full/20/2/573, on Mar. 3, 2008].
PACS: Picture archiving and communication systems in biomedical imaging, HK Huang, Copyright 1996. Table Contents; pp. 396–401.
Picture Archiving and Communication Systems (PACS) in Medicine, Huang et al., Copyright 1991.
GE Medical Systems Technical Publications, Direction 2246811–100, Revision 2, Senographe 2000 D Acquisition Workstation Conformance Statement for DICOM V3.0, latest Copyright 2000.
Solicitation for Digital Imaging Network—Picture Archiving and Communication System, Jan. 21, 1997.

MedImage Software Modules Brochure, Aug. 12, 1997, pp. 1–9.
Hipax Medical Imaging and Communication System Version 3 User Instruction Manual, Sep. 1999.
Product Showcase, "Automated DICOM Exchange Station" (Sorna Product Announcement), Medical Imaging Magazine, vol. 15, No. 1, Jan. 2000, p. 72.
PacsCube User ManualInstallation Guide Version 4.1, © 2006, pp. 1–63.
Steinhart Medizinsysteme, Product Information: Hipax System: Medical Image Processing and Communication.
Steinhart Medizinsysteme, Hipax Multi–Monitor System.
"Security, ASP, Systems Integration to Highlight PACS Exhibits (Agfa through Amicas)," AuntMinnie.com, dated Nov. 26, 2000.
"Security, ASP, Systems Integration to Highlight PACS Exhibits (InSiteOne through Rogan)," AuntMinnie.com dated Nov. 16, 2000.
Camtronics, Ltd., Camtronics Medical Systems: Image Workstation: DICOM Conformance Statement: Document No. 09610–0021 (Rev. A), dated Oct. 26, 1999.
Hanlon, W.B., Fener, E.F., and Downs, J.W. "Data Storage and Management Requirements for the Multimedia Computer–based Patient Medical Record," Proceedings of the Fourteenth IEEE Symposium on Mass Storage Systems: Storage—At the Forefront of Information Infrastructures, Sep. 11–14, 1995, pp. 11–16.
Hilbel, T., Reiter, M.A., Brockmeier, K., Kuecherer H.F., Haass, M., "Advantages of a Cardiac DICOM Network Server/Writer for Viewing and Permanent CD–R Archiving of Cardiovascular X–Ray Angiography Images," Computers in Cardiology, 2000, pp. 649–652, vol. 27.
Saha, S., "The New Age Electronic Patient Record System," Proceedings of the 1995 Fourteenth Southern Biomedical Engineering Conference, Apr. 7–9, 1995, pp. 134–137.
Dimitroff D.C. et al: "An Object Oriented Approach to Automating Patient Medical Records" Proceedings of the International Computer Software And Applications Conference. (Compsac), US, Washington, IEEE. Comp. Soc. Press, vol. Conf. 14, 1990, pp. 82–87.
Kleinholz L. et al: "Multimedia and PACS. Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996 (1996–06), pp. 313–322, XP002083080 1996, Amsterdam, Netherlands, Elsevier, Netherlands ISBN: 0–444–82497–9.
May T.: "Medical Information Security: The Evolving Challenge", 1998, IEEE doc #0–7803–4536–5/98 pp. 85–92.
Cooper T.: "Kaiser Permanente Anticipates High Costs as it Gears Up for HIPPA", IT Heath Care Strategist, vol. 1, No. 10, Oct. 1999, p. 4.
Haufe G. et al.: XP–000914153, PACS at work: A Multimedia E–Mail Tool for the Integration of Images, Voice and Dynamic Annotation, Computer Assisted Radiology, 1996.
Product Showcase: Automated Dicom Exchange Station, Medical Imaging Magazine, Jan. 2000.
VEPRO Medimage Printout, Päediatrische Kardiologie Universitätsklinik Heidelberg: INF 150–153, 69120, dated Jan. 30, 2009.
VEPRO, Centura–Porter Advertist Hospital Training Reports, dated 1999.

Invoice for Centura Health, dated Oct. 1, 1999 and Check from Centura Health to Vepro, dated Oct. 1, 1999.

VEPRO, Purchase Order from Centura Health, date Sep. 30, 1999.

VEPRO, Centura Health Purchase Order Confirmation, dated Sep. 30, 1999.

VEPRO, Serial Number Records for Project Denver, dated Nov. 25, 1999.

VEPRO Computersysteme GmbH, Medimage: DICOM Archiving & Viewing Station, Software Vers. 4.42, User–Manual, dated May 9, 2000.

Engineering Software Releases, Product Release Checklists, and Software Release Notes from Mitra Imaging to Electromed International, dated Sep. 5, 1997 and Sep. 12, 1997.

Medical Imaging web page for Image Archiving the ASAP Way, dated Nov. 2000.

Short Instructions: DICOM Communication by HIPAX, dated 1995–1999.

VEPRO, Product Sheet: Image/Film Jukebox Server, dated Feb. 19, 1999.

VEPRO, Product Sheet: Image/Film Archive Server: dated Feb. 19, 1999.

VEPRO, Diagram of a Digital Cath–Lab, dated Feb. 19, 1999.

VEPRO, Cardio–Network, dated Feb. 19, 1999.

"TDK Launches Innovative Medical DVD/CD Recording Station With Embedded PC," redOrbit.com, dated Sep. 13, 2004.

Business Profile of Algotec: Where the Web PACS the punch, dated Jun. 22, 2000.

Emedia Professional, "The New Dyes Cast: Mapping the CD–R Media Market—Includes Related Articles—Industry Overview," dated Oct. 1998.

"New Products & Services: News Briefs," Health Management Technology, dated Feb. 1, 2000.

AGFA IMPAX Quotation, dated Jun. 8, 1998.

DICOM Conformance Statement, WinSCP32 v2.42 Version 7, dated Nov. 2000.

IMPAX Web 1000 DICOM Web Server Specifications, dated May 30, 1998.

ETIAM, DICOM 3.0 Conformance Statement: DICOM Eye v2.42 Version 1, dated Sep. 12, 2000.

$10^{th}$ Conference on Computer Applications to Assist Radiology and $4^{th}$ Conference on Computer Assisted Radiology, RL Arenson & RM Friedenberg, Symposium Foundation, Copyright 1990, pp. 1–441.

$10^{th}$ Conference on Computer Applications to Assist radiology and $4^{th}$ Conference on Computer Assisted Radiology, RL Arenson & RM Friedenberg, Symposium Foundation, Copyright 1990, pp. 442–791.

11th Conference on Computer Applications in Radiology and 6th Conference on Computer assisted Radiology, William Brody and Gerald Johnston, Copyright 1992, pp. 1–376.

11 th Conference on Computer Applications in Radiology and 6th Conference on Computer assisted Radiology, William Brody and Gerald Johnston, Copyright 1992, pp. 376–434; 445–749.

12th Conference on Computer Applications in Radiology and 8th Conference on Computer Assisted Radiology, Jun. 12–15, 1994, Johannes Boehme & Alan Rowberg, Copyright 1994.

13th Conference on Computer Applications in Radiology, Jun. 6–9, 1996, R Kilcoyne, et al., Copyright 1996.

510(k) summary, Cardiovascular Work Station (CWS) 5000 and CWS 3000, RJ Flatau, dated Oct. 7, 1999.

A five–step approach to digital image manipulation for the radiologist, FM Carl et al., Radiographics Jul.–Aug. 2002 22:4.

A look at infoRAD 1992, infoRAD: Informatics in Radiology, Ackerman, Radiographics Sep. 1992, 12:5.

A low–cost CD–ROM based image archival system, LH Schwartz and SV Lossef, Radiographics Jan. 1995 15:1.

A new approach to teleconferencing with intravascular US and cardiac angiography in a low–bandwidth environment, JN Stahl et al., Radiographics Sep.–Oct. 2000, 20:5.

A PACS RFP toolkit presented to The Fifth RIS–PACS School, Georgetown University Medical Center, JH Perry, dated Feb. 3, 1995.

A PACS RFP toolkit presented to The Seventh RIS–PACS School, Georgetown University Medical Center, JH Perry, dated Aug. 11, 1997.

A Unified Timeline Model and User Interface for Multimedia Medical Databases, JDN Dionisio et al, Computerized Medical Imaging and Graphics 20:4, Jul.–Aug. 1996.

Accessing Picture Archiving and Communication System Text and Image Information Through Personal Computers, MR Ramaswamy et al., Computers in Radiology, AJR 163, Nov. 1994.

ACOM.PC 2.2 DICOM Conformance Statement, Version 1.0, dated Sep. 29, 1999.

Advantanges of a Cardiac DICOM Network Server / Writer for Viewing and Permanent CD–R Archiving of Cardiovascular Angiography Images, Hibel et al, Computers in Cardiology 2000; 27:649–652.

AIM, Advanced informatics in medicine, EurIPACS, European integrated picture archiving & communication system in the hospital, Merheus et al., dated Dec. 31, 1994.

An economical, personal computer–based picture archiving and communication system, T–C Wu et al., Radiographics Mar.–Apr. 1999, 19:2.

Angiocardiography without cinefilm: Information on the new digital imaging interchange standard for cardiology based on DICOM, "Last Updated: Tuesday, Jun. 11, 1996 by Tim Becker.,"

Automated prefetch mechanism: Design and implementation for a radiology PACS, AWK Wong et al., SPIE vol. 2165.

Brigham and Women's teams PACS, RIS technologies—Brigham and Women's Hospital in Boston combines Picture Archival Communication Systems and radiology information systems technologies—Includes related article on imaging technology trends, Rob Hard, dated Mar. 1994.

CD–R & CD–RW: Questions and Answers, OSTA Optical Storage Technology Association, dated Jul. 15, 1997.

CD–Surf User's Guide Version 1.0, Algotec, Copyright 2001.

Clinical Experience with PACS at the University of Pennsylvania, HL Kundel et al., Computerized Medical Imaging and Graphics 15:2, May–Jun. 1991.

Clinical experience with PACS, presented at the Radiological Society of North America $81^{st}$ Scientific Assembly and Annual Meeting Nov. 25–Dec. 1, 1995.

Computer–based radiology information system: From floppy disk to CD–ROM, EF Binet et al., Radiographics 15:5, Sep. 1995.

Computerized scientific exhibit in radiology: A valuable format for delivering scientific information, DGK Varma, et al., Radiographics 14:5, Sep. 1994.

Consulting with radiologist outside the hospital by using java, S–K Lee et al., Radiographics 19:4, Jul. –Aug. 1999.

Cost Savings in a Digital Radiology Department, GM Kolodny et al, dated Mar. 9, 2009, but may be from 1997.

D.I.S.C. 96 (ESC version) ESC annual meeting—Birmingham, T Becker.

DeJarnette Research Systems, DICOM/QR, DICOM Conformance Statement, Copyright 1997.

DeJarnette Research Systems, MediShare 1000 Worklist Manager, DICOM Conformance Statement, Copyright 1995–1996.

DHCP integrated imaging project: Report of the evaluation panel, Department of Veterans Affairs, Jun. 8, 1990.

DICOM Conformance Requirements for CT/MR Modalities, Version 1.0, dated Nov. 15, 1999.

DICOM Media Interchange Standards for Cardiology: Initial Interoperability Demonstration, Elion, Copyright 1995.

DICOM Structured Reporting, David Clunie, Copyright 2000.

Digital archive system for radiology images, AWK Wong, et al., Radiographics 14:5, Sep. 1994.

Digital case library: A resource for teaching, learning, and diagnosis support in radiology, KJ Macura et al., Radiographics 15:1, Jan. 1995.

Digital Imaging and Communications in Medicine (DICOM Supplement 19 General Purpose CD–R Image Interchange Profile, dated Jan. 28, 1997.

Digital Imaging and Communications in Medicine (DICOM) Supplement 40: DVD–RAM Media Application Profiles, dated May 18, 2001.

Digital networking and archiving with ACOM TOP, W Sallfrank, International Journal of Cardiac Imaging 14:323–327, 1998.

Distributing medical images with internet technologies: A DICOM java viewer, J Fernandez–Bayo et al., Radiographics 20:2, Mar.–Apr. 2000.

Editorial, Wong and Huang, Computerized Medical Imaging and Graphics 20:4, Jul.–Aug. 1996.

Entwicklung von Algorithmen und Programmen für ein Archivierungs– und Kommunikationssystem zur internetbasierten Verwaltung medizinischer Bilder, Khludov, Sergey, Aug. 1999.

Evaluating PACS Success: A Multidimensional Model, G Pare et al., Proceedings of the 38$^{th}$ Hawaii International Conference on System Science, Copyright 2005.

Evolution of the clinical review station for enterprise–wide multimedia radiology reporting, W Hanlon et al., Proc. Of SPIE vol. 3980, PACS Design and Evaluation: Engineering and Clinical Issues, dated Feb. 2000.

Fast nearest neighbor search in medical image databases, F Korn et al., Proceedings of the 32$^{nd}$ VLDB Conference, 1996.

Filmless digital radiology—feasibility and 20 month experience in clinical routine, H Mosser et al., Medical Informatics, 19:2, 1994.

Final Text—Supplement 2, Digital Imaging and Communications in Medicine (DICOM), Part II: Media Storage Application Profiles, Addenda on Conformance, dated Feb. 26, 1995.

Final Text—Supplement 3—Part 12, Digital Imaging and Communications in Medicine (DICOM), Part 12: Media Format and Physical Media for Media Interchange, dated Feb. 26, 1995.

Finding the path: A worldwide web–based guide for imaging evaluation of patiens in the emergency department, LM Azmoun et al., Radiographics 17:1, Jan.–Feb. 1997.

First DIN–PACS award goes to IBM as Computer Giant Wins Portsmouth Bid, web.archive.org date "Apr. 15, 2001."

GE Medical Systems Technical Publications, IIS FP10282, Revision I, PathSpeed PACS Version 8.0 Conformance Statement for DICOM V3.0, Dated Sep. 2000.

Hospital integrated picture archiving and communication systems: A second generation PACS concept, M Osteaux, Copyright 1992.

Image archives and image data bases: How do they differ?, CC Jaffe, Radiographics 14:3, May 1994.

ImagiNet Workflow and Management Manual Version 3.0, Algotec, Copyright 2003.

Implementation of the DICOM 3.0 Standard: A pragmatic Handbook, Robert Hindel, Copyright 1994.

Implementing a DICOM—HL7 interface application, SL Fritz et al., SPIE vol. 2435.

Information management and distribution in a medical picture archive and communication system, FW Prior, Copyright 1992.

Inside BringhamRAD: Providing radiology teaching cases on the internet, GL Mammome et al., Radiographics 15:6, Nov. 1995.

Integrating a Personal–Computer Local–Area Network with a Radiology Information System: Value as a Tool for Clinical Research. MS Frank et al., Computers in Radiology, AJR 162, Mar. 1994.

Integrating the healthcare enterprise: A primer: Part 4. The role of existing standards In IHE, M Henderson et al., Radiographics 21:6, Nov.–Dec. 2001.

Interactive Multimedia in the High Performance Organization: Wealth Creation in the Digital Economy, David Ticoll, Copyright 1995.

Interfacing the PACS and the HIS: Results of a 5–year implementation, TV Kinsey, Radiographics, May–Jun. 2000;20(3):883–91.

Legacy System Integration Using Web Technology, RL Kennedy et al, Proc. Of SPIE vol. 3980, PACS Design and Evaluation: Engineering and Clinical Issues, dated Feb. 2000.

Lockheed Martin Operating Instructions, Vantage Picture Archiving and Communication System, 5.0 Release, dated Aug. 1996.

Med–e–Mail Technical Manual version 1.0, Algotec, Copyright 2001.

Medical image database: a content–based retrieval approach, Tagare et al., J Am Med Inform Assoc. 1997.

MediLink Technical Manual Version 1.5, Algotec, Copyright 2001.

MediPrime DICOM Conformance Statement, Algotec, Latest Copyright 2000.

MediStore Technical Manual Version 1.1, Algotec, Copyright 1999.

Medweb Image Server DICOM Conformance Statement, Revision 2.1, dated Jul. 1, 1998.

Merge Connectivity Products: MergeArk, "webarchive.org" date "Sep. 16, 2000".

MergeWorks: A system of flexible building blocks that provide DICOM infrastructure for electronic image management, MergeTechnologies, Inc., "webarchive.org" date "Dec. 2, 1998."

MergeWorks: Store, MergeTechnologies, Inc., "webarchive.org" date "Dec. 3, 1998."

MergeWorks: Datasheets, MergeTechnologies, Inc., "webarchive.org" date "Dec. 3, 1998."

MergeWorks: Print, MergeTechnologies, Inc., "webarchive.org" date "Dec. 3, 1998."

Minutes: Working group 6 (base standard) DICOM standards committee., Dated Jun. 28, 1999.

Mutimedia image and data navigation workstation, O Ratib et al., Radiographics 17:2, Mar.–Apr. 1997.

North by Northwest: Initial Experience with PACS at Northwestern Memorial Hospital, DS Channin et al., Proc. Of SPIE vol. 3980, PACS Design and Evaluation: Engineering and Clinical Issues, dated Feb. 2000.

OSCAR, Optical system for cine archiving and review, dated Feb. 1999.

PACS Databases and Enrichment of the Folder Manager Concept, KP Andriole et al., Journal of Digital Imaging, 13:1, Feb. 2003.

PACS Implementation Experiences: From In–house to Parnership to Advisory Board, HK Huang, Proc. Of SPIE vol. 3980, PACS Design and Evaluation: Engineering and Clinical Issues, dated Feb. 2000.

PACS mini refresher course: Electronic imaging workstations: Ergonomics issues and the user interface, SC Horii, Radiographics 12:4, Jul. 1992.

PACS mini refresher course: Evaluation of requirements and planning for picture archiving and communication system, JC Honeyman et al., Radiographics 12:1, Jan. 1992.

PACS mini refresher course: Image archival technologies, MM Frost et al., Radiographics 12;2, Mar. 1992.

PACS mini refresher course: Introduction to the ACR–NEMA DICOM Standard, WD Bidgood & SC Horii, Radiographics 12:2, Mar. 1992.

PACS mini refresher course: Local area network topologies, media, and routing, BK Stewart., Radiographics 12:3, May 1992.

PACS mini refresher course: Network and ACR–NEMA DICOM protocols, SC Horii & WD Bidgood, Radiographics 12:3, May 1992.

PACS mini refresher course: Picture archiving and communication systems: An overview, RH Choplin et al., Radiographics 12:1, Jan. 1992.

PACS mini refresher course: Software suite for image archiving and retrieval, SR Seshadri et al., Radiographics 12:2, Mar. 1992.

PACS mini refresher course: System Integration: Requirements for a fully functioning electronic radiology department, JM Boehme II and RH Choplin, Radiographics 12:4, Jul. 1992.

PACS mini refresher course: Three methods of implementing a picture archiving and communcation system, HK Huang, Radiographics 12:1, Jan. 1992.

PACS mini refresher course: Wide area network strategies for teleradiology system, SJ Dwyer et al., Radiographics 12:3, May 1992.

PACS: Picture archiving and communication systems in biomedical imaging, HK Huang, Copyright 1996, pp. 396–401 and Table of Contents.

Part four: A nontechnical introduction to DICOM, SC Horii, Radiographics 17:5, Sep.–Oct. 1997.

Personal Notes, SNM 96, RE Zimmerman, dated Mar. 9, 2009, but may be from 1996.

Picture Archiving and Communication System (PACS): a Progressive Approach with Small Systems, M Osteaux et al., European Journal of Radiology 22 (1996) 166–174.

Project DEPRAD (Deployable Radiology and Teleradiology System) in Bosnia/Hungary, SK Mun, Report Date Mar. 1997.

Radiology and computer science, LV Ackerman, Radiographics 11:6, Nov. 1991.

RadNotes: A novel software development tool for radiology education, AB Baxter et al., Radiographics 17:3, May–Jun. 1997.

Research and development progress report, UCLA medical imaging division PACS / Teleradiology, dated Feb. 1995.

Selections from: A generic hospital PACS RFP presented to the Seventh RIS–PACS School, Georgetown University Medical Center, JH Perry, Dated Jul. 9, 1997.

Selections from: Picture Archiving and Communication Systems (PACS) in Medicine, Huang et al., Copyright 1991.

Siemens DICOM 3.0 Conformance Statement, DICOMLink v1.2 for ICON, Copyright 1998.

Siemens SIENET DICOM Conformance Statement MagicView 300 Version VA30A, Revision 8.0, Copyright 2000.

Siemens, SIENET MagicView 300, Copyright Apr. 2001.

The All–Digital Department Moves to the Web, L. Barbaras et al., Clinical Data on the WWW, Copyright 1996, posted Jul. 12, 1996.

The Evolution of Electronic Imaging in the Medical Environment, BJ Erickson and NJ Hangiandreou, Journal of Digital Imagining, 11:3, Supp 1, Aug. 1998.

UCSF Radiological Informatics Research: A Progress Report, Feb. 1996.

UCSF Radiological Informatics Research: A Progress Report, Feb. 1997.

Using a Kodak Photo CD Technology for Preservation and Access: A Guide for Librarians, Archivists, and Curators, AR Kenney and OY Reiger, dated as "Web links confirmed as of Apr. 30, 1998."

Using Experience with Bidirectional HL7—ACR–NEMA Interfaces between the Federal Government HIS/RIS and Commericial PACS to Plan for DICOM, Peter M/ Kuzmak et al., SPIE vol. 2435.

Web Technology and its Relevance to PACS and Teleradiology, W DeJarnette, Applied Radiology, dated Aug. 2000.

IMAGEAXS, Pro–Med 4.01, "Read Me," dated Aug. 20, 1998.

VEPRO Computersysteme GmbH, "Cardio–Viewing Station," dated 1997.

VEPRO Computersysteme GmbH, "Readme," dated Sep. 16, 1997.

Mediface, "PiView™ 3.0 User's Guide, part 1" dated Sep. 1999.

Mediface, "PiView™ 3.0 User's Guide, part 2" dated Sep. 1999.

Mediface, "PiView™ 3.0 User's Guide, part 3" dated Sep. 1999.

Mediface, PiView 3.0 (3.0.7.0) English Version, "Read-Me.txt," dated Nov. 10, 1999.

Mediface, PiView 3.0, "DICOM Conformance Statement, Rev. 1.2–990903," dated 1999.

ACR Learning File Sampler 1 (32-bit), Help File, dated 1999.

VOXAR, Plug'n View 3d 2.1 (Demonstration), "readme.txt," dated Nov. 12, 1999.

Medical Imaging Technology Associates, Tapestry Release Notes, dated May 8, 1997.

Medical Imaging Technology Associates, Tapestry Read Me, dated May 9, 1997.

Medical Imaging Technology Associates, Preliminary Tapestry Users Guide, dated 1997.

Medical Imaging Technology Associates, Tapestry Version 1.0 Medical Image Review Software Demonstration, dated Jan. 1997.

ALGOTECH, CDSurf, Help File, dated 1999.

MEDVISION, VisiTran-MD, Screen Captures, dated 1997.

OSIRIS, OSIRIS Imaging Software User Manual, Version 3.1, dated 1996.

DICOM Birmingaham 96, Tutorial Rev. 3.0, dated 1996.

American Society of Echocardiography, DICOM Demonstration, Toronto, Canada, dated Jun. 14–16, 1995.

ICMIT, DICOM Development Project , dated Jun. 19, 1996.

DICOM 3.0 Public Doman Software, dated Dec. 21, 1995.

ICMIT, DICOM Development Project: What is DICOM Anyway?, dated Dec. 18, 1995.

ICMIT, Patient Information Folder Project, dated Jul. 4, 1996.

ICMIT, Patient Information Folder Project Demonstration, dated Sep. 11, 1996.

Areeda Associates, SeeMor Medical Image Viewing Software for Windows 95/NT and Macintosh, "Readme.txt," dated Nov. 17, 1997.

Areeda Associates, SeeMor Users Manual, dated 1997.

GE Medical Systems, Radiological Society of North America, "Press Information: Destination Digital," dated 1999.

GE Medical Systems, "Press Information: GE Medical Systems Launches New Enterprise–Wide Services Offering for Health Care Providers: CompareCare to Promote Productivity and Simplification of Equipment Services Hospital–Wide," dated Nov. 28, 1999.

GE Medical Systems, "Press Information: GE Medical Systems Redesigns Customer–Driven Service Business for the New Millennium," Nov. 28, 1999.

GE Medical Systems, "Press Information: GE Medical Systems Demonstrates World–Wide CT System Featuring Premium GE Technology: GE CT/e System to Provide Doctors, Patients Around the World With Access to State–of–the–Art GE CT Imaging Equipment," dated Nov. 28, 1999.

GE Medical Systems, "Press Information: GE Medical Systems Expands CT HISPEED Product Line: Introduces Faster Scanner and Mobile System to Make State–of–the–Art CT Technology Product Line Even Stronger," dated Nov. 28, 1999.

GE Medical Systems, "Press Information: LightSpeed QX/i: One Year Later: Breakthrough Multi–Slice CT Scanner Continues to Enhance Productivity Through New Technology, Improved Clinical Applications," dated Nov. 28, 1999.

GE Medical Systems, "Press Information: GE Medical Systems Provides Comprehensive Solutions to Help Health Care Providers Make Digital Transformation: GE's Full–Service Digital Solutions Promote Hospital–Wide Productivity, Patient Health Care Accessability," dated Nov. 28, 1999.

GE Medical Systems, "Press Information: GE Medical Systems' Digital Chest X–Ray System Increases Physician Productivity, Improves Speed of Exams," dated Nov. 28, 1999.

GE Medical Systems, "Press Information: Revolution XR/d Filmless X–Ray Table Enables Timely Patient Diagnosis and Treatment," dated Nov. 28, 1999.

GE Medical Systems, "Press Information: GE Medical Systems Expands Portfolio of Online Productivity Solutions Available to Health Care Providers," dated Nov. 28, 1999.

GE Medical Systems, "Press Information: GE Healthcare Financial Services Announces Innovative Online Offerings to Boost Hospital and Clinic Productivity," dated Nov. 28, 1999.

GE Medical Systems, "Press Information: GE Medical Systems Strengthens Commitment to Women's Health Care herSource Offerings: Global Leader in Health Care Services Provides More Solutions for Women's Health and Well–Being," dated Nov. 28, 1999.

GE Medical Systems, "Press Information: GE Medical Systems Introduces Advanced Mammography System with New Patented GE X–Ray Tube: System Reduces Radiant Exposure by 40 Percent," dated Nov. 28, 1999.

GE Medical Systems, "Press Information: GE Medical Systems' Integrated Imaging Solutions Demonstrates Advanced Internet Imaging Technologies at RSNA 1999," dated Nov. 28, 1999.

GE Medical Systems, "Press Information: GE Medical Systems' Integrated Imaging Solutions Introduces Advantage Workstation 4.0," dated Nov. 28, 1999.

GE Medical Systems, "Press Information: GE Medical Systems' Integrated Imaging Solutions Announce Pathspeed Release 8.0," dated Nov. 28, 1999.

GE Medical Systems, "Press Information: GE Medical Systems' Integrated Imaging Solutions Announces Advanced Analysis Capabilities on Pathspeed," dated Nov. 28, 1999.

GE Medical Systems, "Press Information: GE Medical Systems' Integrated Imaging Solutions Introduces Pathspeed Extend," dated Nov. 28, 1999.

GE Medical Systems, "Press Information: GE Medical Systems' Integrated Imaging Solutions Announces Pathspeed Prism: Software Integrates Patient Information in One Application," dated Nov. 28, 1999.

GE Medical Systems, "Press Information: GE Medical Systems Introduces Advanced Patient Imaging Archive System To Help Hospitals Go Digital: State–of–the Art System Archives Patient Data Immediately; Promotes Better Access to Health Care," dated Nov. 28, 1999.

GE Medical Systems, "Press Information: Smaller Hospitals Get The Bigger Picture With GE Medical Systems' State–Of–The–Art Image Distribution System," dated Nov. 28, 1999.

GE Medical Systems, "Press Information: New Volume Analysis Software From GE Medical Systems Allows Fast, Simple Analysis Of Diagnostic Images On The GE Advantage Workstation," dated Nov. 28, 1999.

GE Medical Systems, "Press Information: GE Medical Systems Introduces First Medical Imaging Software To Let Doctors 'Drive Around' Inside Patient Anatomy: First Generation Interactive MRI Software Lets Doctors do Real–Time Studies as Patients Breathe and Move," dated Nov. 28, 1999.

GE Medical Systems, "Press Information: GE Medical Systems Expands Mobile Offerings Through Cardiac MR Scanner: SIGNA CV/i Now Available in a Mobile Configuration," dated Oct. 18, 1999.

GE Medical Systems, "Press Information: GE Increases Power Of MR Imaging With New Gradient Platforms: New Gradients Deliver Power and Speed," dated Nov. 28, 1999.

GE Medical Systems, "Press Information: GE Medical Systems Introduces MR Technology To Help Physicians Obtain Chemical Information From The Brain: New Information to Supplement MRI Images of Brain to Help Guide Biopsies," dated Nov. 28, 1999.

GE Medical Systems, "Press Information: Six Sigma Quality Design Leads to Faster Exams: GE Medical Systems Introduces Breakthrough 'Open' MRI System," Nov. 17, 1999.

GE Medical Systems, "Press Information: gemedicalsystems.com Offers New MR Technology For Sale Via Internet: Live Demonstrations to be Broadcast Daily from Radiology Community's Largest Trade Show," dated Nov. 28, 1999.

GE Medical Systems, "Press Information: GE Medical Systems Brings All–In–One Nuclear Cardiac Software To GE Workstations: 'Emory Cardiac Toolbox' Gives Physicians Greater Access to Patient Data," dated Nov. 28, 1999.

GE Medical Systems, "Press Information: GE Medical Systems Introduces New Breakthrough Medical Imaging Procedure," dated Sep. 30, 1999.

GE Medical Systems, "Press Information: GE Medical Systems First To Introduce High Performance Cancer Detecting Scanner For Mobile Services: Mobile Leader Makes Popular 'PET' Imaging Technology Accessible to Doctors, Patients Globally," dated Nov. 28, 1999.

GE Medical Systems, "Press Information: GE Medical Brings Six Sigma Quality To Customers," dated Nov. 28, 1999.

GE Medical Systems, "Press Information: AmeriNet And GE Medical Systems Sign National Contract For Ultrasound Systems," dated Oct. 26, 19999.

GE Medical Systems, "Press Information: GE Medical Systems Introduces Advance 'Smart' Ultrasound System," dated Nov. 28, 1999.

GE Medical Systems, "Press Information: Introduction Accelerated by Six Sigma Quality: GE Introduces Breakthrough Ultrasound Technology; LOGIQ 700 Expert Series Offers Potential To Better Diagnose Stroke Risks," dated Apr. 29, 1999.

GE Medical Systems, "Press Information: GE Medical Systems Makes New Advanced Ultrasound Systems Affordable For Smaller Hospitals And Clinics: Medical Profession Embraces GE's Development of High–Tech Systems," dated Nov. 28, 1999.

GE Medical Systems, "Press Information: GE Medical Systems Wins $1.4 Million Order To Provide State–of–the–Art Ultrasound Suite At Massachusetts General Hospital," dated Nov. 28, 1999.

GE Medical Systems, "Press Information: GE Medical Systems Signs Five–Year Agreement With Navix Radiology Systems, Inc.," dated Nov. 28, 1999.

GE Medical Systems, "Press Information: GE Medical Systems Introduces Revolutionary X–Ray Technology: GE Advantx LCA+ System Helps Treat Blood Vessel Diseases Linked to Heart Attacks and Strokes," dated Nov. 28, 1999.

GE Medical Systems, "Press Information: GE Medical Systems Unveils New Biplane X–Ray System," dated Nov. 28, 1999.

GE Medical Systems, "Press Information: GE Medical Systems Introduces New Tool To Aid In Minimally Invasive Surgeries," dated Nov. 28, 1999.

GE Medical Systems, GE Press Info—radiological Society of North America, Images, dated 1999.

Analogic, SuperDASM Configuration Keywords: A White Paper Engineering Document, Rev. 2, dated Jul. 13, 1998.

RDI, Cobrascan, Presentation dated 1999.

RDI, Cobrascan, Xscan32 Imaging Software, Version 2.10, Users' Guide, dated 1999.

Midasys Digital Systems, DxWin 2.0 Evaluation Version, "Readme.txt," dated 1997.

1996 Annual HIMSS Conference and Exhibition, Managing Care: The Race Is On, dated Mar. 3–7, 1996.

William J. Ahrens and Gerard M. Nussbaum, "The Help Desk and the Integrated Clinical Information System," 1996 Annual HIMSS Conference and Exhibition.

Brian L. Cassel, "Definiting the Future Managed Care Information Requirements," 1996 Annual HIMSS Conference and Exhibition.

Leland B. Cross, Jr., "Setting the Stage—The Risks of Integration," 1996 Annual HIMSS Conference and Exhibition.

Rhonda Delmater, "Multi–Media Messaging: An Emerging Vision for Health Care Delivery," 1996 Annual HIMSS Conference and Exhibition.

Cheryl L. Fontenot, "A Phased Approached to Value–Added Voice Processing," 1996 Annual HIMSS Conference and Exhibition.

Gail S. Gulinson, "Transforming the Health Care System Through Health Data Networking," 1996 Annual HIMSS Conference and Exhibition.

Jan M. Kastens, RN, M.S., "Hospital Information Systems Approaches Do Not Work for Integrated Health Care Delivery," 1996 Annual HIMSS Conference and Exhibition.

Shelly Miller, "Selecting and Implementing Local Facilities and Services from Competitive Providers," 1996 Annual HIMSS Conference and Exhibition.

Mel Van Howe, M.B.A., "Introducing Managed Care Applications Into An Integrated Delivery System," 1996 Annual HIMSS Conference and Exhibition.

Tom B. Wilson, Ph.D., "Healthcare Handoffs Across a Wide Area: A Groupware Solution," 1996 Annual HIMSS Conference and Exhibition.

Carol Boston and Linus Diedling, "Clinical Process Reengineering: Process, Potential And Pitfalls," 1996 Annual HIMSS Conference and Exhibition.

Grace A. O'Neil, RN, BS, and Kath Uyeda, Ph.D., "Early Prototyping: Birth Of An Ambulatory Care System User Interface," 1996 Annual HIMSS Conference and Exhibition.

Michael E. Bettinger, "Tracking Critical Patient Information With A Social Work Activity Database," 1996 Annual HIMSS Conference and Exhibition.

Linda Reeder, "Linking Outcomes—Based Documentation And Clinical Pathways With Automated Functions," 1996 Annual HIMSS Conference and Exhibition.

Michael A. Torres et al., "A Comprehensive Emergency Services Assessment," 1996 Annual HIMSS Conference and Exhibition.

Michael J. Hafner, "Effectiveness Of Device Locations In The UIHC's Computerized Charting System," 1996 Annual HIMSS Conference and Exhibition.

James R. Prescott, PE, "What's The Score And How Much Time Is Left?," 1996 Annual HIMSS Conference and Exhibition.

Edward I. Walkley, MD, "Data–Based Assessment Of Urgent Care In A Pediatric ED," 1996 Annual HIMSS Conference and Exhibition.

Richard L. Brandon and John Robinette, "Redesign Of Decedent Care System Provides Compassion, Responsiveness, And Security," 1996 Annual HIMSS Conference and Exhibition.

Richard J. Linderman, "Reengineering Transcription Services To Reduce Costs And Improve Service Quality," 1996 Annual HIMSS Conference and Exhibition.

Cynthia McKinney and Susan Brockhaus, "Benefits of Cost Accounting Within a Multihospital System," 1996 Annual HIMSS Conference and Exhibition.

Christopher N. Smith, "Staffing and Patient Classification in a Post Anesthesia Care Unit," 1996 Annual HIMSS Conference and Exhibition.

Robert Copple, PE, et al., "Developing a Methodology to Drive Patient Care Unit Consolidation," 1996 Annual HIMSS Conference and Exhibition.

James L. Smith, III, et al., "Laboratory Redesign: Life After Cap Units," 1996 Annual HIMSS Conference and Exhibition.

Stephen M. Smith, Cpt., "Mailed Appointment Reminders: An Analysis Of Their Cost–Effectiveness," 1996 Annual HIMSS Conference and Exhibition.

Sara Lafrance, "Security vs. Access: A New Health Care Dilemma," 1996 Annual HIMSS Conference and Exhibition.

Mark Gross and Philip M. Lohman, "Technology And Tactics Of Physician Integration," 1996 Annual HIMSS Conference and Exhibition.

John D. Morgan, et al., "Building An Information Infrastructure: Practical Lessons From Three Multifacility Health Care Enterprises," 1996 Annual HIMSS Conference and Exhibition.

R. L. (Vern) Davenport, et al., "Understanding And Assessing CHIN Network Technology," 1996 Annual HIMSS Conference and Exhibition.

Dennis Winstein, et al., "Optimizing Clinical Information Systems In Complex Computing Environments," 1996 Annual HIMSS Conference and Exhibition.

Lucy Molfetas, "Strategic CPR Issues: Benchmarking Paper Documentation Prior To Implementation," 1996 Annual HIMSS Conference and Exhibition.

Mary Jean Barrett, RN, BSN, MBA, et al., "Concept To Reality: Strategic Approach For Supporting Managed Care Needs," 1996 Annual HIMSS Conference and Exhibition.

Donald P. Huebner and Lilian R. Miller, "Business Process Reengineering Of An Outpatient Clinic Using Simulation," 1996 Annual HIMSS Conference and Exhibition.

Philip A. Katz, "Improving Competitive Position By Use Of The Computerized Patient Record And Associated Technologies," 1996 Annual HIMSS Conference and Exhibition.

Mark H. Biddle, Esq., et al., "Integrating Telecommunications Systems Into The Evolving Health Care Delivery Environment," 1996 Annual HIMSS Conference and Exhibition.

Colleen M. Prophet, et al., "On The 'Paperless Trail'—A Computerized Charting System," 1996 Annual HIMSS Conference and Exhibition.

Brian M. Paige, "Information Warehousing In The Integrated Delivery System," 1996 Annual HIMSS Conference and Exhibition.

Marsha A. Sutter and James A. Baker, "Redesigning The Medication Management System," 1996 Annual HIMSS Conference and Exhibition.

Kevin J. Dombkowski, et al., "Using Electronic Data Interchange In Managed Care Performance Measurement," 1996 Annual HIMSS Conference and Exhibition.

Clement J. McDonald, MD, "Implementing A Physician Order Entry System: Perspective From Five Physicians," 1996 Annual HIMSS Conference and Exhibition.

Jagdish Kohli, PhD, et al., "Distributed Architecture For A Wide–Area Medical Image Repository," 1996 Annual HIMSS Conference and Exhibition.

Jeffery S. Blair, "An Overview Of Health Care Information Standards," 1996 Annual HIMSS Conference and Exhibition.

Ralph T. Wakerly, et al., "Planning For The Four Stages Of Health Information Network Development," 1996 Annual HIMSS Conference and Exhibition.

William F. Andrew, ME, PE, et al., "The Computer–Based Patient Record: An Essential Technology For Healthcare," 1996 Annual HIMSS Conference and Exhibition.

Thomas G. Tape, MD, et al., "Designing A Clinician User–Interface For A Health Care Information System," 1996 Annual HIMSS Conference and Exhibition.

Harry E. McQueen, Jr. and Kate Manzone, "Enabling HMO Product Implementation Through Improved Work Processes And Technology," 1996 Annual HIMSS Conference and Exhibition.

Donald E. Schildkamp and John A. Callahan, "OR Team Learns While Improving Stock And Reprocessing Workflow," 1996 Annual HIMSS Conference and Exhibition.

Mitchell S. Curtis and Austin Brown, "The Role Of Information Systems In Medicaid Managed Care," 1996 Annual HIMSS Conference and Exhibition.

Sallie Williams, et al., "The Inside Story On Chin Implementation: CIO's First Hand Experience," 1996 Annual HIMSS Conference and Exhibition.

W. Brent Peterson, "Strategies For Ambulatory Care Scheduling," 1996 Annual HIMSS Conference and Exhibition.

Leslie A. Scholten and Jon C. Hubble,"Automated Nursing Supply Stations—Gold Mine Or Fool's Gold," 1996 Annual HIMSS Conference and Exhibition.

Faye A. Sisk, PhD and Betsy H. Hampton, RN, BSBA, "Report Cards: Are You Ready For Data Driven Competition," 1996 Annual HIMSS Conference and Exhibition.

Glen Knight, "Project Management For Health Care Professionals," 1996 Annual HIMSS Conference and Exhibition.

Sheldon I. Dorenfest, CPA, MBA, "Emerging Trends In Health Care Information Systems: Increasing Focus On Process Improvement Benefits Through Clinical Automation," 1996 Annual HIMSS Conference and Exhibition.

Jean Ann Larson, "The Reengineering Approach—Techniques And Tools," 1996 Annual HIMSS Conference end Exhibition.

John Glaser, PhD, FHIMSS and Giland Kuperman, MD, PhD, "Impact Of Information Events On Medical Care," 1996 Annual HIMSS Conference and Exhibition.

Elaine Remmlinger and Marc S. Newman, "The Dating Game: Mergers, Affiliations, And Their Information Technology Implications," 1996 Annual HIMSS Conference and Exhibition.

John Lynch, "CHINS: A Collaborative Approach To Outcomes Analysis," 1996 Annual HIMSS Conference and Exhibition.

James C. Benneyan, "Improving Health Care Using SPC And Quality Engineering: Billing And Laboratory Case Studies," 1996 Annual HIMSS Conference and Exhibition.

Mark A. Kaiser et al., "New Information Requirements For The New World Of Managed Health Care," 1996 Annual HIMSS Conference and Exhibition.

Joseph A. Cirillo and Leigh Ann Wise, "Testing The Impact Of Change Using Simulation," 1996 Annual HIMSS Conference and Exhibition.

Gary E. Gamerman, MS, JD, "Development And Implementation Case Study: Cleaning The Legal, Regulatory, And Contractual Barriers," 1996 Annual HIMSS Conference and Exhibition.

Sylvia K. Dowding, "On The Road To Staff Reengineering," 1996 Annual HIMSS Conference and Exhibition.

Jerry L. Mathis et al., "Case Study: A Health Care System's Use Of Wireless Technology," 1996 Annual HIMSS Conference and Exhibition.

Annette Valenta, DrPH et al., "Informatics Education: Evolving Competencies, Continuing Discussions," 1996 Annual HIMSS Conference and Exhibition.

Harm J. Scherpbier, MD et al., "Aspects Of Knowledge Sharing Using The Arden Syntax," 1996 Annual HIMSS Conference and Exhibition.

Deborah Kohn, MPH, RRA et al., "Mail And Messaging Software: M&Ms Of Communications—A Treat For Health Care Information Systems," 1996 Annual HIMSS Conference and Exhibition.

Wayne M. Gray, FHIMSS et al., "Planning And Developing Of A Statewide Health Information Network," 1996 Annual HIMSS Conference and Exhibition.

Dave Niemeyer et al., "The Good, The Bad And The Usable—A Clinical Worstation," 1996 Annual HIMSS Conference and Exhibition.

James Kazmer et al., "The Creation Of A Virtual Electronic Medical Record" 1996 Annual HIMSS Conference and Exhibition.

Thomas H. Hendershott, "Evaluating Process Change Proposals In An Outpatient Pharmacy Using Simulation," 1996 Annual HIMSS Conference and Exhibition.

Janet B. Wu et al., "Wireless Data Transmission: How To Implement Remote Data–Acess," 1996 Annual HIMSS Conference and Exhibition.

Martha B. Tecca and Robert Garrett, "Radical Operating Improvement—A Rational Approach For Ongoing Results," 1996 Annual HIMSS Conference and Exhibition.

Arvind P. Kumar, FHIMMS et al., "Transforming Organization Structures To Implement Integrated Delivery Systems," 1996 Annual HIMSS Conference and Exhibition.

Landen Bain et al., "The Benefits And Implications Of A Statewide Health Information Network For A Major Medical Center," 1996 Annual HIMSS Conference and Exhibition.

Richard B. H. Graham and Karen K. Geisler, "Achieving Results: Implementation Of Best Practices In Patient Financial Services," 1996 Annual HIMSS Conference and Exhibition.

Linda L. Nice and Gregory M. Archual, "A Team Uses Simulation And Benchmarking To Improve Radiology Performace," 1996 Annual HIMSS Conference and Exhibition.

G. James Blaine, et al., "project Spectrum: Technology Alliance For The Emerging Integrated Health System," 1996 Annual HIMSS Conference and Exhibition.

Ronald L. Johnson, "Trends In The Health Care Vendor Marketplace," 1996 Annual HIMSS Conference and Exhibition.

Thomas W. Smith and Loren N. Jacobson, "Are You Really Ready For CHINs?," 1996 Annual HIMSS Conference and Exhibition.

Stan Wiebe, "Information Systems Planning For An Urban/Rural Integrated Delivery System," 1996 Annual HIMSS Conference and Exhibition.

Erica Drazen and Jane Metzger, "Creating New Models For Ambulatory Practice: Efficient, Wellness–Focused, IT–Enabled," 1996 Annual HIMSS Conference and Exhibition.

David L. Kimball, "The Information Technology Leader's Role In Renewing The Healthcare Enterprise," 1996 Annual HIMSS Conference and Exhibition.

Cindy D. Spurr, et al., "Automating Critical Pathways—One Hospital's Experience," 1996 Annual HIMSS Conference and Exhibition.

J. Craig Klimczak and Kenneth Bopp, "Reengineering Medical Records With A Text Archive And Retrieval System," 1996 Annual HIMSS Conference and Exhibition.

Leigh Ann Wise and Paul D. Mermelstein, "A Managed Care Demand Model For Ambulatory Care Services," 1996 Annual HIMSS Conference and Exhibition.

William P. Vrooman, et al., "Benefits Realization Analysis Of A Clinical Information System," 1996 Annual HIMSS Conference and Exhibition.

Robert Bowman, et al., "Building And Maintaining Today's Networks," 1996 Annual HIMSS Conference and Exhibition.

Arvind M. Salvekar, et al., "Community–Wide Implementation Of Quality Outcome Measurements And Patient Satisfaction Report," 1996 Annual HIMSS Conference and Exhibition.

Edward F. Sweeney, et al., "Successful Implementation Of Procedural Outcome And Disease State Management Databases," 1996 Annual HIMSS Conference and Exhibition.

Rosemary Nelson, et al., "Outcomes of Telemedicine Services . . . Patient And Medicolegal Issues," 1996 Annual HIMSS Conference and Exhibition.

Betsy S. Hersher, et al., "The CIO's Position In Today's Emerging Health Care System: Lessons Learned," 1996 Annual HIMSS Conference and Exhibition.

Richard I. Skinner, et al., "Ambulatory Information Systems For Managed Care," 1996 Annual HIMSS Conference and Exhibition.

Rudy J. Crespin, et al., "Establishing World Wide Web Presence: Guidelines For Health Care Organizations," 1996 Annual HIMSS Conference and Exhibition.

Michael G. Bissell and William E. Miller, "Reengineering Laboratory Operations," 1996 Annual HIMSS Conference and Exhibition.

Judy Hager and Cindy Hartless, "Reengineering Laboratory Operations," 1996 Annual HIMSS Conference and Exhibition.

Richard P. Corley, et al., "Infrastructure Requirements For Rapidly Changing Hospital Delivery Systems," 1996 Annual HIMSS Conference and Exhibition.

Pamela K. Wear, et al., "Building Security Models For Patient Identifiable Health Information," 1996 Annual HIMSS Conference and Exhibition.

Ed Spires and Gene Nacey, "Discharge Process Streamlined Through Interactive Voice Response Technology," 1996 Annual HIMSS Conference and Exhibition.

Michael C. Longo and Pete Lockhart, "Structured Cabling: Foundations For The Future," 1996 Annual HIMSS Conference and Exhibition.

William H. Crawford, et al., "EIS Unplugged,," 1996 Annual HIMSS Conference and Exhibition.

Richard A. Crabtree, "Pay For Extra Performance," 1996 Annual HIMSS Conference and Exhibition.

Verda Weston, et al., "Reengineering And Technology—Building A Strong Foundation For The CPR," 1996 Annual HIMSS Conference and Exhibition.

Kenneth Weiner and George E. Levesque, "This Hospital's Like A Hotel!," 1996 Annual HIMSS Conference and Exhibition.

M. Jafar Asadi and William A. Baltz, "Clinical Pathways Costing: The Key To Profitability—An Example To Improve Cost And Efficiency Using Activity–Based Costing," 1996 Annual HIMSS Conference and Exhibition.

Gerald M. Nussbaum, "Protecting The Net: Leveraging The Infrastructure," 1996 Annual HIMSS Conference and Exhibition.

James E. Farstad, et al., "Operations, Facilities And Communications: Understanding Success Factors In Patient–Centered Care," 1996 Annual HIMSS Conference and Exhibition.

John R. Kludt, et al., "Rebounding From Rejection: Reintroducing Physicians To Your IS," 1996 Annual HIMSS Conference and Exhibition.

Jeffrey W. Muscarella and John Hoben, "Delivering Information Services Via The World Wide Web," 1996 Annual HIMSS Conference and Exhibition.

Karen Hartmann, et al., "Integrating Clinical Decision Support Technology To Existing Hospital Information Systems," 1996 Annual HIMSS Conference and Exhibition.

Tracey D. Holden, et al., "Nuts And Bolts Approach To Project Management," 1996 Annual HIMSS Conference and Exhibition.

Steve Neal and Cynthia L. Brown, "Case Study: Interactive Video Communications In Health Care," 1996 Annual HIMSS Conference and Exhibition.

Cynthia McKinney, et all, "Simplifying The Approach To Productivity Monitoring," 1996 Annual HIMSS Conference and Exhibition.

Edward Barthell, et al., "The National Information Infrastructure Health Information Network NII–HIN," 1996 Annual HIMSS Conference and Exhibition.

AREEDA Associates, "Welcome to the SeeMor Demo CD," dated 1999.

AREEDA Associates, SeeMor Version 3, "Windows 9X/2000/NT4 Users Manual," dated 1999.

AREEDA Associates, SeeMor, Demo CD ReadMe.txt File, dated Nov. 11, 1999.

Diforum Series, "Soft–Copy Interpretation: How To Do It, What to Avoid," Diagnostic Imaging, pp. 66–72, dated Sep. 1998.

James Brice, "PACS Integration: Radiology's Portal to Both Magic and Misery," Diagnostic Imaging, pp. P30–P42, dated Sep. 1998.

Michael J. Cannavo, "Commentary: PACS and TeleRadiology: Who Pays the Bill?," Diagnostic Imaging, pp. P15–P17, dated Sep. 1998.

John C. Hayes, "Imaging News: Data Shows Filmless Imaging Saves in High–Volume Setting," Diagnostic Imaging, pp. 9–13, dated Jul. 1998.

Stephen M. Pomerantz, M.D., "First Person: Soft–Copy Interpretation Finally Surpasses Film," Diagnostic Imaging, pp. 37–39, dated Mar. 1998.

James Brice, "Cover Story: In Search of Smart & Simple PACS Workstations," Diagnostic Imaging, pp. 42–46, dated Mar. 1998.

Michael J. Cannavo, "PACS Integration: Info Network Integrates Islands of Automation," Diagnostic Imaging, pp. 25–27, dated Feb. 1998.

Philip G. Drew, Ph.D., "Signal–to–Noise: Surveys Attest to Growing Interest in PACS," pp. 21–22, dated Jan. 1998.

Steven C. Horii, M.D., "Informatics: Workstation Priorities: Automation, Integration," Diagnostic Imaging, pp. 40–45, dated Jan. 1998.

Diane Shindoll, "Cover Story: Managing Risk in Planning and Implementing a PACS," Diagnostic Imaging, pp. 46–51, dated Jan. 1998.

Kathy Kincade, "Digital Processing: Wavelets Challenge JPEG in Image Compression," Diagnostic Imaging, pp. 125–127, dated Nov. 1997.

Sridhar B. Seshadri, "Market Scan: PACS Market Migrates to 'Early Majority' Users," Diagnostic Imaging, pp. 207–211, dated Nov. 1997.

Bernard F. King, Jr., M.D., "Conversion Process: Calculates Film Costs Before Going Electronic," Diagnostic Imaging, pp. P47–P50, dated Sep. 1997.

Emily Hayes, "Case Study: PACS helps Mayo Practice Meet Urgent–Care Needs," Diagnostic Imaging, pp. P22–P24, dated Sep. 1997.

"PACS Market Moves at Brisk Pace as Interest in Technology Grows," PACS & Networking News, vol. 2, No. 5, pp. 1–3, dated May 1998.

"RSNA, HIMSS Join Forces to Sponsor Systems Integration," PACS & Networking News, vol. 2, No. 4, p. 1, dated Apr. 1998.

Sohard AG, Radin Version 2.0, dated Nov. 2002, Screen Captures.

VEPRO, MedImage Cardio Viewing Station Extended, Version 4.41.05, "About Cardio Viewing Station," dated 1999.

VEPRO, MedImage Cardio Viewing Station Extended, Version 4.41.03, "About Cardio Viewing Station," dated 1998.

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9, 15, 16 and 21 are determined to be patentable as amended.

Claims 10-14, 17-20 and 22, dependent on an amended claim, are determined to be patentable.

Claims 1-8 and 23-27 were not reexamined.

9. A system comprising:
a medical image server configured to receive medical image data that is generated by a plurality of imaging modalities, the medical image data being formatted in a standard medical imaging format used by specialized computers configured for viewing medical images;
a database configured to store medical image data generated by the plurality of imaging modalities;
a plurality of browsing terminals configured to receive a user selection that defines selected medical image data;
a search module configured to search the database for related medical image data that is related to the selected medical image data; and
a production station that is configured to record all of the following onto a *single, portable* data storage medium:
the selected medical image data, recorded in the standard medical imaging format,
the related medical image data, recorded in the standard medical imaging format, and
a viewing program that is configured to allow viewing of the selected and the related medical image data that is recorded onto the data storage medium on widely accessible computers not specifically configured with standard medical imaging software for viewing of medical images.

16. A method for selecting and automatically recording medical image data onto a data storage medium, the method comprising:
receiving medical image data from a plurality of imaging modalities, the received medical image data being formatted in a standard medical imaging format used by specialized computers configured for viewing medical images;
storing the received medical image data in a database;
providing a user interface configured to receive a user selection that defines selected medical image data;
searching the database for related medical image data that is related to the selected medical image data;
recording the selected medical image data and the related medical image data onto a *single, portable* data storage medium using a production station, the selected medical image data being recorded on the data storage medium in the standard medical imaging format;
recording a viewing program onto the data storage medium using the production station, the viewing program being configured to allow viewing of medical image data stored on the data storage medium on widely accessible computers not specifically configured with standard medical imaging software for viewing of medical images;
printing a label using the production station, wherein the label includes identifying information associated with the selected medical image data; and
affixing the label to the data storage medium using the production station.

21. [The method of claim 16.] *A method for selecting and automatically recording medical image data onto a data storage medium, the method comprising:*
*receiving medical image data from a plurality of imaging modalities, the received medical image data being formatted in a standard medical imaging format used by specialized computers configured for viewing medical images;*
*storing the received medical image data in a database;*
*providing a user interface configured to receive a user selection that defines selected medical image data;*
*searching the database for related medical image data that is related to the selected medical image data;*
*recording the selected medical image data and the related medical image data onto a data storage medium using a production station, wherein the data storage medium is an optical disk*[.]*, the selected medical image data being recorded on the data storage medium in the standard medical imaging format;*
*recording a viewing program onto the data storage medium using the production station, the viewing program being configured to allow viewing of medical image data stored on the data storage medium on widely accessible computers not specifically configured*

15. [The system of claim 9.] *A system comprising:*
*a medical image server configured to receive medical image data that is generated by a plurality of imaging modalities, the medical image data being formatted in a standard medical imaging format used by specialized computers configured for viewing medical images;*
*a database configured to store medical image data generated by the plurality of imaging modalities;*
*a plurality of browsing terminals configured to receive a user selection that defines selected medical image data;*
*a search module configured to search the database for related medical image data that is related to the selected medical image data; and*
*a production station that is configured to record all of the following onto a data storage medium, wherein the data storage medium is an optical disk*[.] *:* with standard medical imaging software for viewing of medical images;

printing a label using the production station, wherein the label includes identifying information associated with the selected medical image data; and affixing the label to the data storage medium using the production station.

* * * * *